(12) United States Patent
Mattoussi et al.

(10) Patent No.: US 9,790,329 B2
(45) Date of Patent: Oct. 17, 2017

(54) PHOTOLIGATION OF AN AMPHIPHILIC POLYMER WITH MIXED COORDINATION PROVIDES COMPACT AND REACTIVE QUANTUM DOTS

(71) Applicant: The Florida State University Research Foundation, Inc., Tallahassee, FL (US)

(72) Inventors: Hedi Mattoussi, Tallahassee, FL (US); Wentao Wang, Tallahassee, FL (US); Goutam Palui, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 366 days.

(21) Appl. No.: 14/672,462

(22) Filed: Mar. 30, 2015

(65) Prior Publication Data
US 2015/0284493 A1    Oct. 8, 2015

Related U.S. Application Data

(60) Provisional application No. 61/974,122, filed on Apr. 2, 2014.

(51) Int. Cl.
*C08F 8/32* (2006.01)
*C08G 81/02* (2006.01)
(Continued)

(52) U.S. Cl.
CPC .............. *C08G 81/025* (2013.01); *C08F 8/32* (2013.01); *C09D 123/36* (2013.01);
(Continued)

(58) Field of Classification Search
None
See application file for complete search history.

(56) References Cited

U.S. PATENT DOCUMENTS

| 2005/0032929 A1 | 2/2005 | Greener |
| 2005/0201974 A1 | 9/2005 | Schestopol et al. |
| 2011/0300096 A1* | 12/2011 | Greener .................. C08F 8/00 424/78.2 |

OTHER PUBLICATIONS

Yildiz, Langmuir, 2010, 26(13), 11503-11511.*
(Continued)

*Primary Examiner* — Robert C Boyle
(74) *Attorney, Agent, or Firm* — Armstong Teasdale LLP

(57) ABSTRACT

The disclosure is directed to multi-coordinating polymers as ligands that combine two distinct metal-chelating groups, lipoic acid and imidazole, for the surface functionalization of QDs. These ligands combine the benefits of thiol and imidazole coordination to reduce issues of thiol oxidation and weak binding affinity of imidazole. The ligand design relies on the introduction of controllable numbers of lipoic acid and histamine anchors, along with hydrophilic moieties and reactive functionalities, onto a poly(isobutylene-alt-maleic anhydride) chain via a one-step nucleophilic addition reaction. We further demonstrate that this design is fully compatible with a novel and mild photoligation strategy to promote the in-situ ligand exchange and phase transfer of hydrophobic QDs to aqueous media under borohydride-free conditions. Ligation with these polymers provides highly fluorescent QDs that exhibit great long-term colloidal stability over a wide range of conditions.

17 Claims, 9 Drawing Sheets

(51) Int. Cl.
  C09D 123/36    (2006.01)
  C09D 187/00    (2006.01)
  G01N 33/50     (2006.01)
  G01N 33/58     (2006.01)
  C09D 135/00    (2006.01)

(52) U.S. Cl.
  CPC ..... *C09D 187/005* (2013.01); *G01N 33/5005* (2013.01); *G01N 33/582* (2013.01); *C09D 135/00* (2013.01)

(56) References Cited

OTHER PUBLICATIONS

Na, ACS Nano, 2012, 6(1), pp. 389-399.*
Na, Hyon Bin et al., "Multidentate Catechol-Based Polyethylene Glycol Oligomers Provide Enhanced Stability and Biocompatibility to Iron Oxide Nanoparticles" Article, ACS Nano, 2012, pp. 389-399, vol. 6, No. 1.
Alivisatos, A.P., Semiconductor Clusters, Nanocrystals, and Quantum Dots, Science; Feb. 16, 1996, vol. 271, No. 5251; ProQuest; pp. 933-937.
Murray, C. B., et al., Synthesis and Characterization of Monodisperse Nanocrystals and Close-Packed Nanocrystal Assemblies, Annu. Rev. Mater. Sci, 2000, vol. 30 pp. 545-610.
Klimov, V.I. et al., Optical Gain and Stimulated Emission in Nanocrystal Quantum Dots, Science, Oct. 13, 2000, vol. 290, No. 5490; ProQuest, pp. 314-317.
Malko, A.V. et al., From amplified spontaneous emission to microring lasing using nanocrystal quantum dots solids, Applied Physcis Letters, Aug. 12, 2002, vol. 81, No. 7, pp. 1303-1305.
Nozik, A. J. et al., Semiconductor Quantum Dots and Quantum Dot Arrays and Applications of Multiple Exciton Generation to Third-Generation Photovoltaic Solar Cells, Chem. Rev., 2010, vol. 110, pp. 6873-6890.
Li Ling et al., Highly Efficient CdS Quantum Dot-Sensitized Solar Cells Based on a Modified Polysulfide Electrolyte, Journal of the American Chemical Society, 2011, vol. 133, pp. 8458-8460.
Raymo, Francisco M., et al., Luminescent chemosensors based on semiconductor quantum dots, Physical Chemistry Chemical Physics, Feb. 1, 2007, vol. 9, pp. 2036-2043.
Medintz, Igor L., et al., Quantum dot bioconjugates for imaging labelling and sensing, Nature Materials, Jun. 2005, vol. 4, pp. 435-446.
Michalet, X. et al., Quantum Dots for Live Cells, in Vivo Imaging, and Diagnostics, Science, Jan. 28, 2005, vol. 307, pp. 538-544.
Biju, Vasudevanpillai et al., Delivering quantum dots to cells: bioconjugated quantum dots for targeted and nonspecific extracellular and intracellular imaging, Chemical Society Reviews, May 27, 2010, vol. 39, pp. 3031-3056.
Zrazhevskiy, Paul et al., Designing multifunctional quantum dots for bioimaging, detection, and drug delivery, Chemical Society Reviews, Dec. 23, 2009, vol. 39, pp. 4326-4354.
Pinaud, Fabien et al., Probing cellular events, one quantum dot at a time, Nature Methods, Apr. 2010, vol. 7, No. 4, pp. 275-285.
Jaiswal, Jyoti K. et al., Long-term multiple color imaging of live cells using quantum dot bioconjugates, Nature Biotechnology, Jan. 2003, vol. 21, pp. 47-51.
Gao, Xiaohu, et al., In vivo cancer targeting and imaging with semiconductor quantum dots, Nature Biotechnology, Aug. 2004, vol. 22, No. 8, pp. 969-976.
Rossetti, R. et al., Size effects in the excited electronic states of small colloidal CdS crystallites, Journal of Chemical Physics, 1984, vol. 80, pp. 4464-4469.
Murray, C. B. et al., Synthesis and Characterization of Nearly Monodisperse CdE (E=S, Se, Te) Semiconductor Nanocrystallites, American Chemical Socity, 1993, vol. 115, pp. 8706-8715.
Dabbousi, B. O. et al., (CdSe)Zns Core-Shell Quantum Dots: Synthesis and Characterization of a Size Series of Highly Luminescent Nanocrystallites, 1997, vol. 101, pp. 9463-9475.

Liu, Wenhao et al., Compact Biocompatible Quantum Dots Functionalized for Cellular Imaging, Journal of American Chemical Society, 2008, vol. 130, pp. 1274-1284.
Susumu, Kimihiro et al., Multifunctional ligands based on dihydrolipoic acid and polyethylene glycol to promote biocompatibility of quantum dots, Nature Protocols, 2009, vol. 4, No. 3, pp. 424-436.
Jung, Jongjin et al., Selective Inhibition of Human Tumor Cells through Multifunctional Quantum-Dot-Based siRNA Delivery, Angew. Chem. Inc. Ed., 2010, vol. 49, pp. 103-107.
Liu, Wenhao et al., Compact Biocompatible Quantum Dots via RAFT-Mediated Synthesis of Imidazole-Based Random Copolymer Lignad, American Chemical Society, 2010, vol. 132, pp. 472-483.
Lee, Jae-Hyun et al., Artificially engineered magnetic nanoparticles for ultra-sensitive molecular imaging, Jan. 2007, vol. 13, No. 1, pp. 95-99.
Stewart, Michael H. et al., Multidentate Poly(ethylene glycol) Ligands Provide Colloidal Stability to Semiconductor and Metallic Nanocrystals in Extreme Conditions, Journal of American Chemical Society, 2010, vol. 132, pp. 9804-9813.
Muro, Eleonora et al., Small and Stable Sulfobetaine Zwitterionic Quantum Dots for Functional Live-Cell Imaging, Journal of American Chemical Society, 2010, vol. 132, pp. 4556-4557.
Lees, Emma E. et al., Experimental Determination of Quantum Dot Size Distributions, Ligand Packing Densities, an Bioconjugation Using Analytical Ultracentrifugation, American Chemical Society, 2008, vol. 8, No. 9, pp. 2883-2890.
Liu, Lu et al., Bifunctional Multidentate Ligand Modified Highly Stable Water-Soluble Quantum Dots, Inorganic Chemistry, American Chemical Society, 2010, vol. 49, pp. 3768-3775.
Clapp, Aaron R. et al., Capping of CdSe—ZnS quantum dots with DHLA and subsequent conjugation with proteins, Nature Protocols, 2006, vol. 1, No. 3, pp. 1258-1266.
Qu, Lianhua et al., Alternative Routes toward High Quality CdSe Nanocrystals, American Chemical Society, 2001, vol. 1, No. 6, pp. 333-337.
Mei, Bing C., Modular poly(ethylene glycol) ligands for biocompatible semiconductor and gold nanocrystals with extended pH and ionic stability, J. Mater. Chem., 2008, vol. 18, pp. 4949-4958.
Uyeda, Tetsuo H. et al., Synthesis of Compact Multidentate Ligands to Prepare Stable Hydrophilic Quantum Dot Fluorophores, Journal of American Chemical Society, 2005, vol. 127, pp. 3870-3878.
Choi, Chung Hang J., et al., Mechanism of active targeting in solid tumors with transferrin-containing gold nanoparticles, PNAS, Jan. 19, 2010, vol. 107, No. 3, 1235-1240.
Clapp, Aaron R. et al., Fluorescence Resonance Energy Transfer Between Quantum Dot Donors, Journal of American Chemical Society, 2004, vol. 126, pp. 301-310.
Medintz, Igor L., et al., Proteolytic activity monitored by fluorescence resonance energy transfer through quantum-dot-peptide conjugates, Nature Materials, Jul. 2006, vol. 5, pp. 581-589.
Chen, Chun-Yen et al., Potassium ion recognition by 15-crown-5 functionalized CdSe/ZnS quantum dots in H2O, Chem. Commun, 2006, pp. 263-265.
Susumu, Kimihiro et al., Colloidal Quantum Dots: Synthesis, Photophysical Properties, and Biofunctionalization Strategies, Atrech House, Aug. 25, 2008, pp. 1-26.
Hines, Margaret A., et al., Synthesis and Characterization of Strongly Luminescing ZnS-Capped CdSe Nanocrystals, J. Phys. Chem, American Chemical Society, 1996, vol. 100, No. 2, pp. 468-471.
van Embden, Joel et al., Mapping the Optical Properties of CdSe/CdS Heterostructure Nanocrystals: The Effects of Core Size and Shell Thickness, Journal of American Chemical Society, 2009, vol. 131, pp. 14299-14309.
Gerion, Daniele, et al., Synthesis and Properties of Biocompatible Water-Soluble Silica-Coated CdSe/ZnS Semicondutor Quantum Dots, J. Phys. Chem. B, 2001, vol. 105, pp. 8861-8871.
Bhang, Suk Ho et al., Hyaluronic Acid-Quantum Dot Conjugates for In Vivo Lymphatic Vessel Imaging, American Chemical Society, May 28, 2009, vol. 3, No. 6, pp. 1389-1398.

(56) References Cited

OTHER PUBLICATIONS

Yildiz, Ibrahim et al., Biocompatible CdSe—ZnS Core-Shell Quantum Dots Coated with Hydrophilic Polythiols, American Chemical Society, 2009, vol. 25, No. 12, pp. 7090-7096.

Yildiz, Ibrahim et al., Biocompatible CdSe—ZnS Core-Shell Quantum Dots with Reactive Function Groups on Their Surface, Langmuir, 2010, vol. 26, No. 13, pp. 11503-11511.

Shen, Hongyan et al., Poly(ethylene glycol) Carbondiimide Coupling Reagents for the Biological and Chemical Functionalization of Water-Soluble Nanoparticles, American Chemical Society, 2009, vol. 3, No. 4, pp. 915-923.

Anderson, Robin E. et al., Systematic Investigation of Preparing Biocompatible, Single, and Small ZnS-Capped CdSe Quantum Dots with Amphiphilic Polymers, American Chemical Society, 2008, vol. 2, No. 7, pp. 1341-1352.

Bullen, C. et al., The Effects of Chemisorption on the Luminescence of CdSe Quantum Dots, Langmuir, 2006, vol. 22, pp. 3007-3013.

Munro, Andrea M. et al., Quantitative Study of the Effects of Surface Ligand Concentration on CdSe Nanocrystal Photoluminescence, J. Phys. Chem. C, 2007, vol. 111, pp. 6220-6227.

Mei, Bing C. et al., Effects of Ligand Coordination Number and Surface Curvature on the Stability of Gold Nanoparticles in Aqueous Solutions, Langmuir, American Chemical Society, 2009, vol. 25, No. 18, pp. 10604-10611.

Na, Hyon Bin et al., Multidentate Catechol-Based Polyethylene Glycol Oligomers Provide Enhanced Stability and Biocompatibility to Iron Oxide Nanoparticles, American Chemical Society, 2012, vol. 6, No. 1, pp. 389-399.

Yu, William W. et al., Forming Biocompatible and Nanaggregated Nanocrystals in Water Using Amphiphilic Polymers, Article, Feb. 20, 2007, pp. 2871-2879, vol. 129, J. Am. Chem. Soc.

Palui, Goutam et al., Poly(ethylene glycol)-Based Multidentate Oligomers for Biocompatible Semiconductor and Gold Nanocrystals, Article, 2011, pp. 2761-2772, vol. 28, Langmuir, American Chemical Society.

Pellegrino, Teresa et al., Hydrophobic Nanocrystals Coated with an Amphiphilic Polymer Shell: A General Route to Water Soluble Nanocrystals, NANO letters, 2004, pp. 703-707, vol. 4, No. 4, American Chemical Society.

\* cited by examiner

PHOTOLIGATION OF AN AMPHIPHILIC POLYMER WITH MIXED COORDINATION PROVIDES COMPACT AND REACTIVE QUANTUM DOTS

CROSS REFERENCE TO RELATED APPLICATIONS

This application claims priority from U.S. Provisional Application Ser. No. 61/974,122 filed Apr. 2, 2014, the disclosure of which is incorporated herein as if set forth in its entirety.

STATEMENT REGARDING FEDERALLY SPONSORED RESEARCH OR DEVELOPMENT

This invention was made with government support under NSF-CHE #1058957 awarded by the National Science Foundation. The government has certain rights in the invention.

FIELD OF THE INVENTION

The present invention relates to a polymer ligand suitable for coordinating with a nanoparticle or a quantum dot.

BACKGROUND OF THE INVENTION

Fluorescent semiconductor nanocrystals (quantum dots, QDs) combine several unique optical and spectroscopic properties that can be tuned via size and/or composition. See References 1-6. For instance, core-shell QDs, such as those made of ZnS-overcoated CdSe nanocrystals, exhibit narrow tunable emission throughout the visible spectrum, combined with high quantum yield and a remarkable resistance to chemical degradation. See References 7-12. These unique features have made them greatly appealing for use as in vivo and in vitro fluorescent probes in a variety of biomedical applications; these include cellular labelling, deep-tissue imaging, biochemical sensing and drug delivery vehicles. See References 11 and 13-27.

Highly fluorescent QDs with good control over size and crystallinity are mostly grown via reduction of organometallic precursors at high temperature and in the presence of hydrophobic coordinating ligands. See References 3, 4, and 7-10. This growth route yields nanocrystals that are only dispersible in organic solvents. A key requirement for a successful integration of these materials into biology is access to an effective and reproducible surface-modification strategy. See References 23 and 28-32. Cap exchange with bifunctional coordinating ligands has been used by several groups to promote the dispersion of various inorganic nanocrystals in buffer media. This strategy relies on the competitive removal of the hydrophobic capping molecules and their replacement with hydrophilic metal-coordinating ligands. See References 23. The strength of the ligand coordination onto the nanocrystal surface along with a strong affinity of the hydrophilic modules to buffer media ultimately control the long term colloidal stability of the QDs in biological environments.

Ligands presenting multiple thiol groups, such as derivates of dihydrolipoic acid (DHLA), greatly enhance the QD colloidal stability in various biological conditions, compared with those presenting mono-thiol or other weakly coordinating groups. See References 33-40. The multi-coordination interactions between the QD and multidentate ligands decrease the ligand dissociation rate from the nanocrystal surfaces, substantially improving the colloidal stability of the QDs in biological media. Nevertheless, thiol-terminated ligands tend to negatively affect the photoluminescence properties of the hydrophilic QDs. See Reference 41. Moreover, under ambient conditions (e.g., room temperature and light exposure) most thiol-based ligands can be affected by photo-oxidation during extended storage time, which cause ligand desorption from the QD surface. See References 28, 42, and 43. This problem becomes more serious at very low concentrations, since the dynamic equilibrium of coordination favors higher dissociation rates. To address some of these limitations, polymer ligands presenting multiple imidazole (or pyridine) groups have been developed as an alternative to thiol groups for coordination on the nanocrystal. See References 42 and 44-47. Imidazole is not affected by this oxidation problem and has been found to potentially enhance the QD emission. See Reference 48. However, imidazole and pyridine exhibit weaker coordination affinity to the nanocrystal surfaces than thiols. For instance, histidine-coated QDs can be easily exchanged by thiol-terminated ligands. See Reference 49. Furthermore, imidazole-based polymer ligands provide hydrophilic QDs that exhibit colloidal stability only in weakly acidic to alkaline pH since the imidazole groups tend to be protonated under acidic conditions (pH<6). See References 44 and 50. This limits their use for common and newer promising conjugation techniques (e.g., EDC coupling and hydrazide reaction are most efficient at pH 4-6). See Reference 51.

The present disclosure refers to the following references by number:
(1) Alivisatos, A. P. *Science* 1996, 271, 933.
(2) Murray, C. B.; Kagan, C. R.; Bawendi, M. G. *Annual Review of Materials Science* 2000, 30, 545.
(3) Peng, Z. A.; Peng, X. G. *Journal of the American Chemical Society* 2001, 123, 183.
(4) Rogach, A. L.; Talapin, D. V.; Shevchenko, E. V.; Kornowski, A.; Haase, M.; Weller, H. *Adv Funct Mater* 2002, 12, 653.
(5) Klimov, V. I. Nanocrystal Quantum Dots, Second Edition 2010, Vii.
(6) Talapin, D. V.; Lee, J. S.; Kovalenko, M. V.; Shevchenko, E. V. *Chemical Reviews* 2010, 110, 389.
(7) Murray, C. B.; Norris, D. J.; Bawendi, M. G. *J Am Chem Soc* 1993, 115, 8706.
(8) Hines, M. A.; Guyot-Sionnest, P. *J Phys Chem-Us* 1996, 100, 468.
(9) Dabbousi, B. O.; RodriguezViejo, J.; Mikulec, F. V.; Heine, J. R.; Mattoussi, H.; Ober, R.; Jensen, K. F.; Bawendi, M. G. *Journal of Physical Chemistry B* 1997, 101, 9463.
(10) Reiss, P.; Bleuse, J.; Pron, A. *Nano Lett* 2002, 2, 781.
(11) Medintz, I. L.; Uyeda, H. T.; Goldman, E. R.; Mattoussi, H. *Nat Mater* 2005, 4, 435.
(12) Resch-Genger, U.; Grabolle, M.; Cavaliere-Jaricot, S.; Nitschke, R.; Nann, T. *Nature methods* 2008, 5, 763.
(13) Bruchez, M.; Moronne, M.; Gin, P.; Weiss, S.; Alivisatos, A. P. *Science* 1998, 281, 2013.
(14) Chan, W. C. W.; Nie, S. M. *Science* 1998, 281, 2016.
(15) Wu, X. Y.; Liu, H. J.; Liu, J. Q.; Haley, K. N.; Treadway, J. A.; Larson, J. P.; Ge, N. F.; Peale, F.; Bruchez, M. P. *Nat Biotechnol* 2003, 21, 452.
(16) Dahan, M.; Levi, S.; Luccardini, C.; Rostaing, P.; Riveau, B.; Triller, A. *Science* 2003, 302, 442.
(17) Gao, X. H.; Cui, Y. Y.; Levenson, R. M.; Chung, L. W. K.; Nie, S. M. *Nature Biotechnology* 2004, 22, 969.

(18) Michalet, X.; Pinaud, F. F.; Bentolila, L. A.; Tsay, J. M.; Doose, S.; Li, J. J.; Sundaresan, G.; Wu, A. M.; Gambhir, S. S.; Weiss, S. *Science* 2005, 307, 538.
(19) Snee, P. T.; Somers, R. C.; Nair, G.; Zimmer, J. P.; Bawendi, M. G.; Nocera, D. G. *J Am Chem Soc* 2006, 128, 13320.
(20) Gill, R.; Zayats, M.; Willner, I. *Angew Chem Int Edit* 2008, 47, 7602.
(21) Yildiz, I.; Deniz, E.; Raymo, F. M. *Chemical Society Reviews* 2009, 38, 1859.
(22) Zrazhevskiy, P.; Sena, M.; Gao, X. H. *Chem Soc Rev* 2010, 39, 4326.
(23) Mattoussi, H.; Palui, G.; Na, H. B. *Adv Drug Deliver Rev* 2012, 64, 138.
(24) Ji, X.; Palui, G.; Avellini, T.; Na, H. B.; Yi, C. Y.; Knappenberger, K. L.; Mattoussi, H. *J Am Chem Soc* 2012, 134, 6006.
(25) Freeman, R.; Willner, I. *Chem Soc Rev* 2012, 41, 4067.
(26) Kay, E. R.; Lee, J.; Nocera, D. G.; Bawendi, M. G. *Angewandte Chemie-International Edition* 2013, 52, 1165.
(27) Probst, C. E.; Zrazhevskiy, P.; Bagalkot, V.; Gao, X. H. *Adv Drug Deliver Rev* 2013, 65, 703.
(28) Zhang, F.; Lees, E.; Amin, F.; Gil, P. R.; Yang, F.; Mulvaney, P.; Parak, W. J. *Small* 2011, 7, 3113.
(29) Chou, L. Y. T.; Ming, K.; Chan, W. C. W. *Chem Soc Rev* 2011, 40, 233.
(30) Sapsford, K. E.; Algar, W. R.; Berti, L.; Gemmill, K. B.; Casey, B. J.; Oh, E.; Stewart, M. H.; Medintz, I. L. *Chemical Reviews* 2013, 113, 1904.
(31) Nam, J.; Won, N.; Bang, J.; Jin, H.; Park, J.; Jung, S.; Jung, S.; Park, Y.; Kim, S. *Adv Drug Deliver Rev* 2013, 65, 622.
(32) Mout, R.; Moyano, D. F.; Rana, S.; Rotello, V. M. *Chem Soc Rev* 2012, 41, 2539.
(33) Susumu, K.; Uyeda, H. T.; Medintz, I. L.; Pons, T.; Delehanty, J. B.; Mattoussi, H. *J Am Chem Soc* 2007, 129, 13987.
(34) Zhan, N.; Palui, G.; Safi, M.; Ji, X.; Mattoussi, H. *J Am Chem Soc* 2013, 135, 13786.
(35) Palui, G.; Na, H. B.; Mattoussi, H. *Langmuir* 2012, 28, 2761.
(36) Liu, W.; Howarth, M.; Greytak, A. B.; Zheng, Y.; Nocera, D. G.; Ting, A. Y.; Bawendi, M. G. *J Am Chem Soc* 2008, 130, 1274.
(37) Stewart, M. H.; Susumu, K.; Mei, B. C.; Medintz, I. L.; Delehanty, J. B.; Blanco-Canosa, J. B.; Dawson, P. E.; Mattoussi, H. *J Am Chem Soc* 2010, 132, 9804.
(38) Giovanelli, E.; Muro, E.; Sitbon, G.; Hanafi, M.; Pons, T.; Dubertret, B.; Lequeux, N. *Langmuir* 2012, 28, 15177.
(39) Yildiz, I.; McCaughan, B.; Cruickshank, S. F.; Callan, J. F.; Raymo, F. M. *Langmuir* 2009, 25, 7090.
(40) Zhu, Z. J.; Yeh, Y. C.; Tang, R.; Yan, B.; Tamayo, J.; Vachet, R. W.; Rotello, V. M. *Nat Chem* 2011, 3, 963.
(41) Bullen, C.; Mulvaney, P. *Langmuir* 2006, 22, 3007.
(42) Liu, W. H.; Greytak, A. B.; Lee, J.; Wong, C. R.; Park, J.; Marshall, L. F.; Jiang, W.; Curtin, P. N.; Ting, A. Y.; Nocera, D. G.; Fukumura, D.; Jain, R. K.; Bawendi, M. G. *J Am Chem Soc* 2010, 132, 472.
(43) Nagaraja, A. T.; Sooresh, A.; Meissner, K. E.; McShane, M. J. *ACS nano* 2013, 7, 6194.
(44) Zhang, P. F.; Liu, S. H.; Gao, D. Y.; Hu, D. H.; Gong, P.; Sheng, Z. H.; Deng, J. H.; Ma, Y. E.; Cai, L. T. *J Am Chem Soc* 2012, 134, 8388.
(45) Han, H. S.; Martin, J. D.; Lee, J.; Harris, D. K.; Fukumura, D.; Jain, R. K.; Bawendi, M. *Angew Chem Int Edit* 2013, 52, 1414.
(46) Viswanath, A.; Shen, Y.; Green, A. N.; Tan, R.; Greytak, A. B.; Benicewicz, B. C. *Macromolecules* 2014, 47, 8137.
(47) Susumu, K.; Oh, E.; Delehanty, J. B.; Pinaud, F.; Gemmill, K. B.; Walper, S.; Breger, J.; Schroeder, M. J.; Stewart, M. H.; Jain, V.; Whitaker, C. M.; Huston, A. L.; Medintz, I. L. *Chemistry of Materials* 2014, 26, 5327.
(48) Medintz, I. L.; Clapp, A. R.; Mattoussi, H.; Goldman, E. R.; Fisher, B.; Mauro, J. M. *Nature Materials* 2003, 2, 630.
(49) Zylstra, J.; Amey, J.; Miska, N. J.; Pang, L.; Hine, C. R.; Langer, J.; Doyle, R. P.; Maye, M. M. *Langmuir* 2011, 27, 4371.
(50) Paiva, T. B.; Tominaga, M.; Paiva, A. C. *Journal of medicinal chemistry* 1970, 13, 689.
(51) Hermanson, G. T. Bioconjugate Techniques, 3rd Edition 2013, 1.
(52) Pellegrino, T.; Manna, L.; Kudera, S.; Liedl, T.; Koktysh, D.; Rogach, A. L.; Keller, S.; Radler, J.; Natile, G.; Parak, W. J. *Nano Lett* 2004, 4, 703.
(53) Yu, W. W.; Chang, E.; Falkner, J. C.; Zhang, J. Y.; Al-Somali, A. M.; Sayes, C. M.; Johns, J.; Drezek, R.; Colvin, V. L. *J Am Chem Soc* 2007, 129, 2871.
(54) Lin, C. A.; Sperling, R. A.; Li, J. K.; Yang, T. Y.; Li, P. Y.; Zanella, M.; Chang, W. H.; Parak, W. J. *Small* 2008, 4, 334.
(55) Lees, E. E.; Nguyen, T. L.; Clayton, A. H. A.; Muir, B. W.; Mulvaney, P. *ACS nano* 2009, 3, 2049.
(56) Janczewski, D.; Tomczak, N.; Han, M. Y.; Vancso, G. J. *Nature Protocols* 2011, 6, 1546.
(57) Diaz, S. A.; Giordano, L.; Jovin, T. M.; Jares-Erijman, E. A. *Nano Lett* 2012, 12, 3537.
(58) Susumu, K.; Mei, B. C.; Mattoussi, H. *Nature Protocols* 2009, 4, 424.
(59) Wang, W.; Ji, X.; Na, H. B.; Safi, M.; Smith, A.; Palui, G.; Perez, J. M.; Mattoussi, H. *Langmuir* 2014.
(60) Palui, G.; Avellini, T.; Zhan, N.; Pan, F.; Gray, D.; Alabugin, I.; Mattoussi, H. *J Am Chem Soc* 2012, 134, 16370.
(61) Bucher, G.; Lu, C. Y.; Sander, W. *Chemphyschem* 2005, 6, 2607.
(62) Tsay, J. M.; Doose, S.; Pinaud, F.; Weiss, S. *J Phys Chem B* 2005, 109, 1669.
(63) Manna, L.; Scher, E. C.; Li, L. S.; Alivisatos, A. P. *J Am Chem Soc* 2002, 124, 7136.
(64) Lee, S. F.; Osborne, M. A. *J Am Chem Soc* 2007, 129, 8936.
(65) Rodriguez-Viejo, J.; Mattoussi, H.; Heine, J. R.; Kuno, M. K.; Michel, J.; Bawendi, M. G.; Jensen, K. F. *Journal of Applied Physics* 2000, 87, 8526.
(66) Pons, T.; Uyeda, H. T.; Medintz, I. L.; Mattoussi, H. *Journal of Physical Chemistry B* 2006, 110, 20308.
(67) Wang, W.; Aldeek, F.; Ji, X.; Zeng, B.; Mattoussi, H. *Faraday discussions* 2014.
(68) Mattoussi, H.; Cumming, A. W.; Murray, C. B.; Bawendi, M. G.; Ober, R. *Phys Rev B* 1998, 58, 7850.
(69) Oh, E.; Susumu, K.; Blanco-Canosa, J. B.; Medintz, I. L.; Dawson, P. E.; Mattoussi, H. *Small* 2010, 6, 1273.
(70) Gravel, E.; Tanguy, C.; Cassette, E.; Pons, T.; Knittel, F.; Bernards, N.; Garofalakis, A.; Duconge, F.; Dubertret, B.; Doris, E. *Chem Sci* 2013, 4, 411.
(71) Delehanty, J. B.; Bradburne, C. E.; Boeneman, K.; Susumu, K.; Farrell, D.; Mei, B. C.; Blanco-Canosa, J. B.; Dawson, G.; Dawson, P. E.; Mattoussi, H.; Medintz, I. L. *Integrative Biology* 2010, 2, 265.
(72) Leatherdale, C. A.; Woo, W. K.; Mikulec, F. V.; Bawendi, M. G. *Journal of Physical Chemistry B* 2002, 106, 7619.

SUMMARY OF THE INVENTION

The present invention is directed to a set of amphiphilic polymers. In some embodiments, a polymer may be prepared by coupling one or both of two metal-chelating groups, thiol (e.g., but not limited to, lipoic acid, LA, or dihydrolipoic acid, DHLA) and imidazole, within the same polymer structure. The resultant polymer is suitable for enhancing overall ligand-to-QD affinity and maintaining high quantum yield, while reducing issues associated with oxidation of the thiol and weak coordination of the imidazole. In some embodiments, the present invention is directed to a set of multi-coordinating and multifunctional polymer ligands that can tightly ligate onto the surface of QDs. Our ligand design relies on the use of a simple one step nucleophilic addition reaction between distinct amine-modified molecules and maleic anhydride groups to introduce large and controllable numbers of, e.g., lipoic acid and imidazole groups along the same polymer backbone. More precisely, amine-terminated lipoic acid, histamine, and poly(ethylene glycol) (PEG) moieties are reacted with poly(isobutylene-all-maleic anhydride) (PIMA) in an organic medium to provide a polymer ligand containing tunable numbers of LAs, imidazoles and PEG moieties. Furthermore, we demonstrate that this ligand design is fully compatible with a novel and mild photoligation strategy to promote the in-situ ligand exchange and phase transfer of QDs to aqueous media under borohydride-free conditions. Ligation of the QDs with these polymers combines the benefits of thiol and imidazole coordination, and provides highly fluorescent QDs that exhibit great long-term colloidal stability over a wide range of conditions, including storage at nanomolar concentration, under ambient conditions, in 100% growth media and in the presence of competing reducing agents. In addition, this strategy provides compact QDs that are suitable for use in energy and charge transfer interactions. We show that incorporating amine reactive groups in the polymer ligand permits covalent conjugation of fluorescent dye and redox active dopamine to the QDs, producing fluorescent platforms where emission can be controlled/tuned by Förster Resonance Energy Transfer (FRET) or via pH-dependent charge transfer (CT) interactions. We also show that these polymer-coated QDs can be easily coupled to cell penetrating peptides (CPP), facilitating intracellular uptake, while eliciting little to no change in the cell viability.

The present invention is therefore directed to a composition comprising a polymer comprising repeat unit (A'), repeat unit (A"), or repeat unit (B), as represented by the following structures:

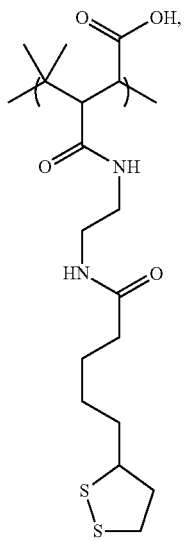

(A')

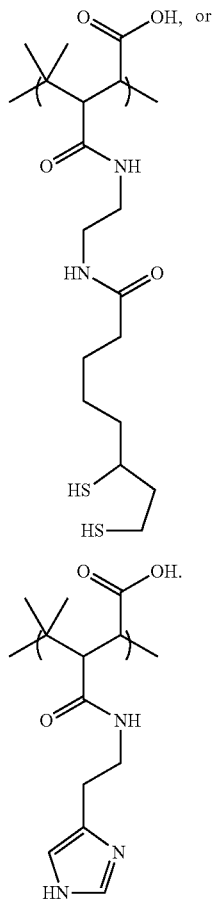

(A")

(B)

The present invention is further directed to a method of preparing a polymer comprising repeat unit (A'), repeat unit (A"), or repeat unit (B), the method comprising contacting poly(isobutylene-all-maleic anhydride) with an amine-containing reactant selected from the group consisting of N-(2-aminoethyl)-4-(1,2-dithiolan-3-yl)pentamide, N-(2-aminoethyl)-6,8-dimercaptooctanoic acid, and histamine.

Other objects and features will be in part apparent and in part pointed out hereinafter.

DESCRIPTION OF THE EMBODIMENT(S) OF THE INVENTION

Figure 1A:
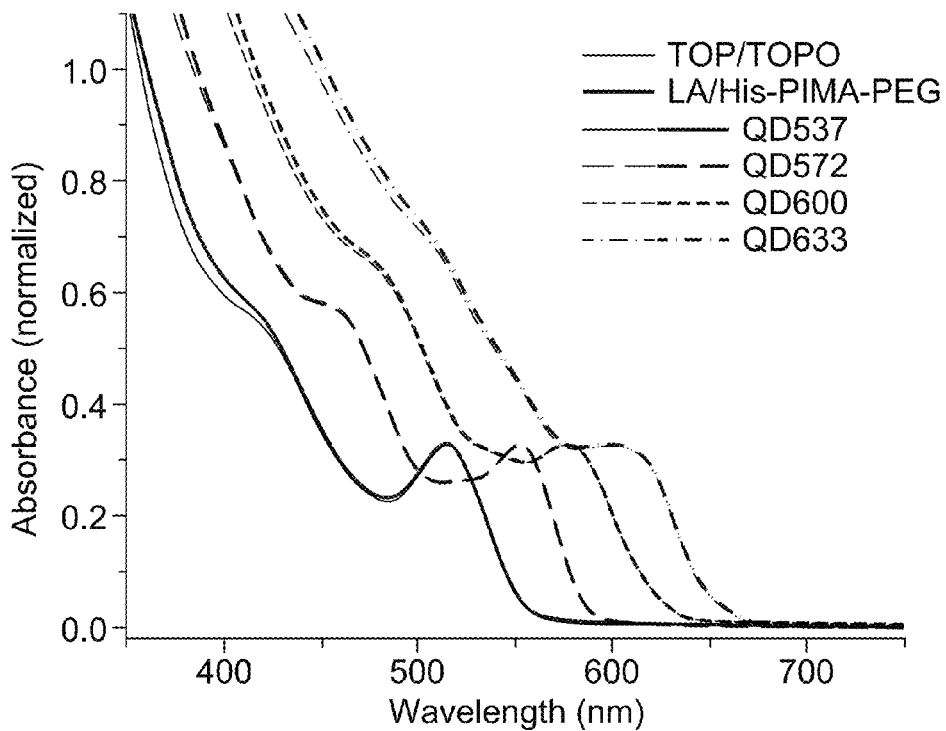
FIG. 1A is a Normalized absorbance spectra of four representative QDs emitting at, from left to right, 537, 572, 600 and 633 nm, before and after photoligation with LA/His-PIMA-PEG ligands.

One aspect of the invention is a multi-coordinating polymer ligand. In some embodiments, the polymer ligand combines at least one of two, preferably both, distinct metal-chelating groups, e.g., but not limited to lipoic acid and imidazole, for the surface functionalization of QDs. These ligands combine the benefits of thiol and imidazole coordination to reduce issues of thiol oxidation and weak binding affinity of imidazole. The ligand design relies on the introduction of controllable numbers of lipoic acid and histamine anchors, along with hydrophilic moieties and reactive functionalities, onto a poly(isobutylene-alt-maleic anhydride) chain via a one-step nucleophilic addition reaction. We further demonstrate that this design is fully compatible with a novel and mild photoligation strategy to promote the in-situ ligand exchange and phase transfer of hydrophobic QDs to aqueous media under borohydride-free conditions. Ligation with these polymers provides highly fluorescent QDs that exhibit great long-term colloidal stability over a wide range of conditions, including a broad pH range (3-13), storage at nanomolar concentration and under ambient conditions, in 100% growth media and in the presence of competing agents with strong reducing property. We further show that incorporating reactive groups in the ligands permits covalent conjugation of fluorescent dye and redox active dopamine to the QDs, producing fluorescent platforms where emission is controlled/tuned by Förster Resonance Energy Transfer (FRET) or pH-dependent charge transfer (CT) interactions. Finally, the polymer-coated QDs have been coupled to cell penetrating peptides to facilitate intracellular uptake, while subsequent cytotoxicity tests showed no apparent decrease in cell viability.

I. Ligand Design.

In some embodiments, polymer ligands are prepared via one-step nucleophilic addition reaction between PIMA and an amine-modified molecule. The amine-modified molecules may be selected from among, but not limited to, lipoic acid-amine (N-(2-aminoethyl)-4-(1,2-dithiolan-3-yl)pentamide), histamine, and PEG-amine. This synthetic scheme has a few unique features. The reaction can be carried out in the absence of coupling reagents or excess precursors, which simplifies purification of the final product(s). The presence of several maleic anhydrides (in some embodiments, ~39) along the backbone allows for the simultaneous insertion of a large but controllable number of distinct and complementary functionalities within the same ligand:lipoic acid and/or imidazole anchoring groups for strong coordination on the QDs, PEG moieties for water solubilization and biocompatibility, and reactive functionalities for targeted conjugation to biomolecules. Additionally, the presence of dimethyl groups between adjacent anhydride rings combined with the cis-trans configuration of the polymer backbone reduces the steric constraints and enhances reactivity, which allows high degrees of substitutions during the addition reaction.

Similar polymer precursors have been used by other groups to design amphiphilic block-copolymers to encapsulate QDs and iron oxide nanoparticles within micelle-like structures. See References 52-57. However, the present ligand design and the surface functionalization strategy are drastically different from the one relying on encapsulation within block-copolymer. Our approach requires the removal of the native cap and involves direct coordination of the new ligands on the QD surfaces. The presence of several metal chelating groups and PEG moieties within the same ligand respectively promote strong coordination on the nanocrystal surface and water solubilization. The multidentate interactions of the polymer ligand yield compact coating, which decreases the hydrodynamic size (compared to encapsulation) and substantially improves the colloidal stability of the final nanocrystals, while allowing surface reactivity.

In some embodiments, the polymer backbone is based on poly(isobutylene-alt-maleic acid). The poly(isobutylene-all-maleic anhydride) (PIMA) platform may comprise between about 10 and about 20,000 repeat units. In general, commercially available PIMA has a number of repeat units between about 10 and about 1000, such as between about 20 and about 100, such as between about 30 and about 50, or between about 35 and about 45, such as about 39. In some embodiments, a commercially-available PIMA having Mw~6 kDa was suitable. See reference 26. The maleic anhydride rings were either fully or partially reacted to provide controlled numbers of side groups bound to the backbone via an amide bond; it also frees several carboxylic groups (as many as the number of maleic anhydride rings present), which can provide additional hydrophilic and potential reactive groups in the final compound. We anticipate that for the molecular weight of approximately 6000 Daltons of polymer reported by the manufacturer the average number of monomers per PIMA chain (or index of polymerization) is equal to 39; a mass for the monomer unit of ~154 g/mol was used. During synthesis, we adjusted the molar amount of each amine-containing moiety with respect to the overall molar amount of monomer units in the precursor polymer.

In some embodiments, the polymer of the present invention is synthesized using poly(isobutylene-alt-maleic anhydride) as a starting reactant and platform. Poly(isobutylene-alt-maleic anhydride) (referred to as PIMA throughout this specification) has the following general structure:

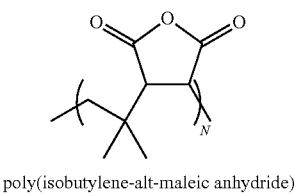

poly(isobutylene-alt-maleic anhydride)

wherein N has a value between about 10 and about 40,000, such as between about 10 and about 20,000, such as between about 10 and about 10,000, or between about 10 and about 5,000. In general, commercially available PIMA has a number of repeat units between about 10 repeat units and about 2000 repeat units, such as between about 20 repeat units and about 1000 repeat units, between about 20 repeat units and about 400 repeat units, such as between about 20 repeat units and about 100 repeat units, such as between about 30 repeat units and about 50 repeat units, or between about 35 repeat units and about 45 repeat units, such as about 39 repeat units. The molecular weight of the PIMA platform may be between about 150 Daltons and about 2,000,000 Daltons, such as between about 300 Daltons and about 800,000 Daltons, or between about 300 Daltons and about 200,000 Daltons, or between about 4500 Daltons and about 70,000 Daltons. A commercially available PIMA has an average Mw of about 165,000 Daltons. Another commercially available PIMA has an average Mw of about 60,000 Daltons. Another commercially available PIMA has an average Mw of about 6000 Daltons. In some embodiments, a commercially available PIMA (Mw, 6000 g/mol; ~39 maleic anhydride monomers per chain) may be selected. According to the present invention, PIMA may be contacted with a reactant comprising a primary and/or secondary amine for nucleophilic coupling to maleic anhydride.

In some embodiments, reactions for nucleophilic coupling of N-(2-aminoethyl)-4-(1,2-dithiolan-3-yl)pentamide (amine-terminated lipoic acid) (Reaction (A')), N-(2-aminoethyl)-6,8-dimercaptooctanoic acid (amine terminated dihydrolipoic acid, or DHLA) (Reaction (A")), and/or histamine (Reaction (B)) to a PIMA chain are shown below.

Reaction (A')

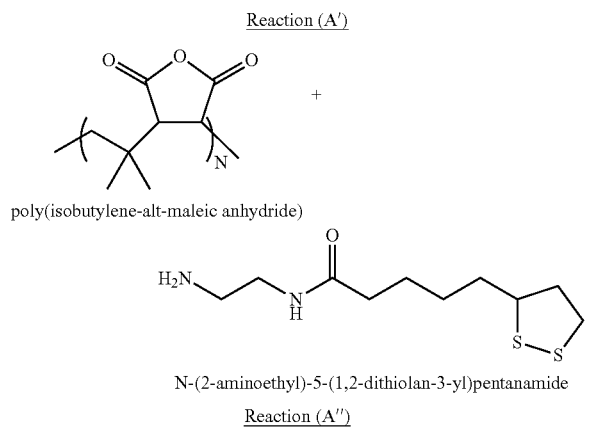

N-(2-aminoethyl)-5-(1,2-dithiolan-3-yl)pentanamide

Reaction (A")

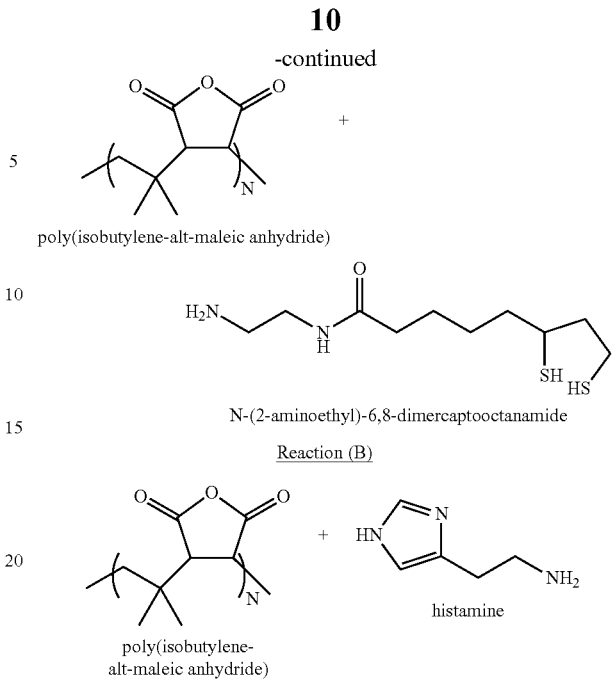

The reaction mixture may comprise PIMA and N-(2-aminoethyl)-4-(1,2-dithiolan-3-yl)pentamide (amine-terminated lipoic acid) and/or N-(2-aminoethyl)-6,8-dimercaptooctanoic acid and/or histamine.

Reaction (A') depicts the reaction between PIMA and N-(2-aminoethyl)-4-(1,2-dithiolan-3-yl)pentamide (amine-terminated lipoic acid) to yield a Repeat Unit (A'), comprising a 1,2-diothiolane ring, having the structure:

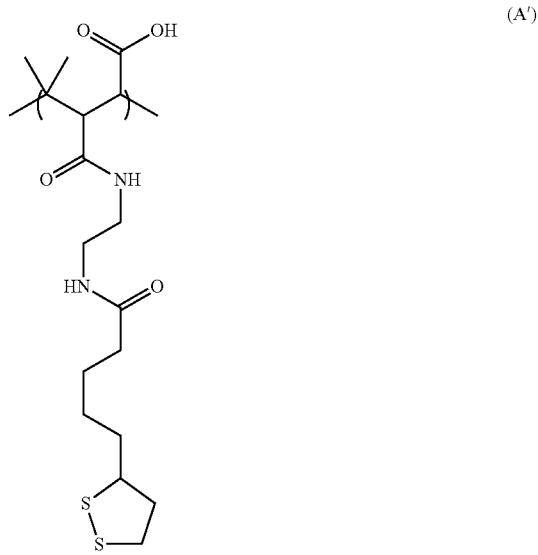

(A')

In some embodiments, PIMA may be reacted with N-(2-aminoethyl)-6,8-dimercaptooctanoic acid (amine terminated dihydrolipoic acid, or DHLA, in which the five-membered ring is open) to yield a Repeat Unit (A") having the structure:

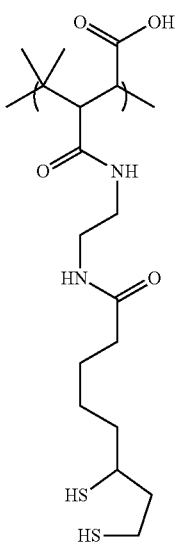

(A")

Repeat unit (A") may also be prepared by oxidizing the 1,2-diothiolane ring of repeat unit (A').

Reaction (B) depicts the reaction between PIMA and histamine to yield a Repeat Unit (B) having the structure:

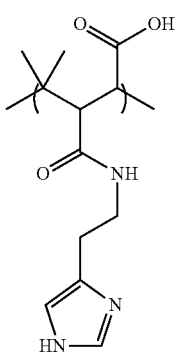

(B)

In some embodiments, the method of the present invention comprises contacting PIMA with N-(2-aminoethyl)-4-(1,2-dithiolan-3-yl)pentamide (amine-terminated lipoic acid) to thereby yield a polymer comprising repeat unit (A'). In some embodiments, the method of the present invention comprises contacting PIMA with N-(2-aminoethyl)-6,8-dimercaptooctanoic acid (amine terminated dihydrolipoic acid, or DHLA) to thereby yield a polymer comprising repeat unit (A"). In some embodiments, the method of the present invention comprising oxidizing the 1,2-diothiolane ring in repeat unit (A') to thereby prepare a polymer comprising repeat unit (A"). In some embodiments, the method of the present invention comprises contacting PIMA with histamine to thereby yield a polymer comprising repeat unit (B). In some embodiments, the method of the present invention comprises contacting PIMA with N-(2-aminoethyl)-4-(1,2-dithiolan-3-yl)pentamide (amine-terminated lipoic acid) and histamine to thereby yield a polymer comprising repeat units (A') and (B). In some embodiments, the method of the present invention comprises contacting PIMA with N-(2-aminoethyl)-6,8-dimercaptooctanoic acid (amine terminated dihydrolipoic acid, or DHLA) and histamine to thereby yield a polymer comprising repeat units (A") and (B). In some embodiments, the method of the present invention comprises contacting PIMA with amine-terminated lipoic acid and/or amine-terminated dihydrolipoic acid to prepare a polymer in which all maleic anhydride units are reacted, or less than all maleic anhydride units are reacted. For example, the reaction mixture may comprise PIMA and N-(2-aminoethyl)-4-(1,2-dithiolan-3-yl)pentamide (amine-terminated lipoic acid) in relative amounts sufficient to react between about 2% and about 100%, between about 10% and about 100%, or between about 20% and about 80%, or between about 30% and about 70% of the maleic anhydride units. In some embodiments, the method of the present invention comprises contacting PIMA with histamine to prepare a polymer comprising repeat units (B) in which all maleic anhydride units are reacted, or less than all maleic anhydride units are reacted. For example, the reaction mixture may comprise PIMA and histamine in relative amounts sufficient to react between about 2% and about 100%, between about 10% and about 100%, or between about 20% and about 80%, or between about 30% and about 70% of the maleic anhydride units. In some embodiments, the reaction mixture may comprise PIMA, amine-terminated lipoic acid, and/or amine-terminated dihydrolipoic aicd, and/or histamine in relative amounts sufficient to react between about 2% and about 100%, between about 10% and about 100%, or between about 20% and about 80%, or between about 30% and about 70% of the maleic anhydride units.

Maleic anhydride that is not coupled with amine-containing reactant may nonetheless undergo ring opening. In some embodiments, therefore, the polymer may additionally comprise a repeat unit that results from ring opening, but not coupling with an amine-containing reactant. In some embodiments, the polymer may comprise a repeat unit (C), having the structure shown below:

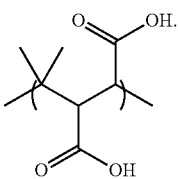

(C)

In some embodiments, the polymer of the present invention may comprise repeat units (A') and/or (A") and (C). In some embodiments, the polymer of the present invention may comprise repeat units (B) and (C). In some embodiments, the polymer of the present invention may comprise some combination of repeat units (A'), (A"), (B), and (C). The molar ratio of lipoic acid reactant and histamine reactant may be between about 4:1 to about 1:4, such as between about 3:1 to about 1:3, such as between about 2:1 to about 1:2, such as about 1:1.

In some embodiments, the polymer of the present invention may comprise repeat units (A') and (C). A polymer comprising repeat units (A') and (C) may have the following structure:

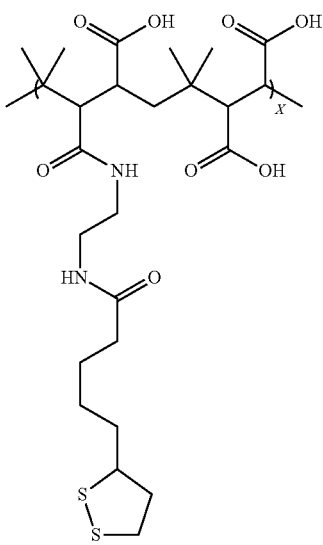

wherein X has a value between about 10 and about 20,000. In some embodiments, X may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units.

In some embodiments, the polymer of the present invention may comprise repeat units (A") and (C). A polymer comprising repeat units (A") and (C) may have the following structure:

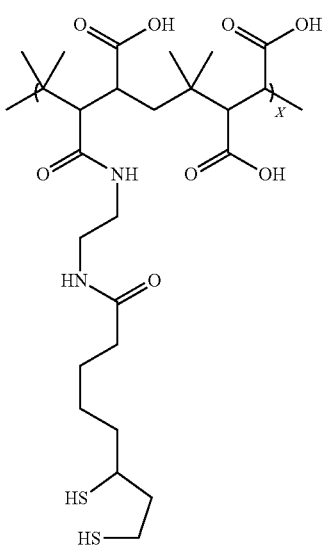

wherein X has a value between about 10 and about 20,000. In some embodiments, X may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units.

In some embodiments, the polymer of the present invention may comprise repeat units (B) and (C). A polymer comprising repeat units (B) and (C) may have the following structure:

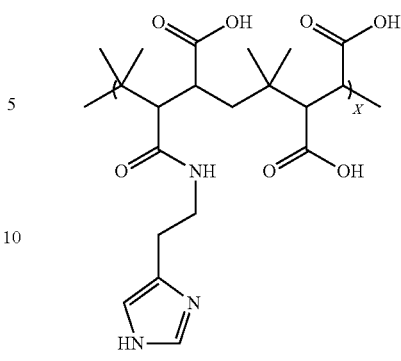

wherein X has a value between about 10 and about 20,000. In some embodiments, X may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units.

In some embodiments, the reaction may incorporate a polyethylene glycol reagent comprising an amine group and a terminal functional group. The synthesis of amine-terminated inert and reactive poly(ethylene glycol) reactant is provided in the examples. In general, a structure of a poly(ethylene glycol) reactant may be as follows:

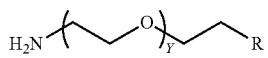

wherein Y has a value between one and about 100 and each R is independently selected from the group consisting of hydroxy (—OH), methoxy (—OCH$_3$), amino (—NH$_2$), azido (—N$_3$), thiol (—SH), lipoic acid, ethynyl (—C≡CH), carboxyl (—COOH), aldehyde (—C(O)H), maleimide, and biotin. In some embodiments, Y may have a value between 5 and about 50, such as between 10 and about 20, such as about 12, or about 15.

In some embodiments, the amine-terminated inert and reactive poly(ethylene glycol) reactant may be capped with methoxy. For example, the PEG precursor may have the structure:

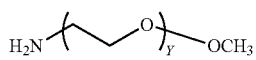

wherein Y has a value between one and about 100. In some embodiments, Y may have a value between 5 and about 50, such as between 10 and about 20, such as about 12, or about 15.

In some embodiments, the amine-terminated inert and reactive poly(ethylene glycol) reactant may be capped with azide. For example, the PEG precursor may have the structure:

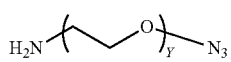

wherein Y has a value between one and about 100. In some embodiments, Y may have a value between 5 and about 50, such as between 10 and about 20, such as about 12, or about 15.

The coupling reaction between an amine-terminated inert and reactive poly(ethylene glycol) precursor and the maleic anhydride moiety of PIMA yields polymer comprising repeat unit (D):

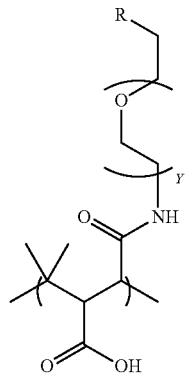

(D)

wherein Y has a value between one and about 100 and each R is independently selected from the group consisting of hydroxy (—OH), methoxy (—OCH$_3$), amino (—NH$_2$), azido (—N$_3$), thiol (—SH), lipoic acid, ethynyl (—C≡CH), carboxyl (—COOH), aldehyde (—C(O)H), maleimide, and biotin. In some embodiments, Y may have a value between 5 and about 50, such as between 10 and about 20, such as about 12, or about 15.

In some embodiments, repeat unit (D) comprises R is methoxy (—OCH$_3$). In some embodiments, repeat unit (D) comprises R is methoxy (—OCH$_3$) and Y is 15. The repeat unit (D) may have the following structure (D'):

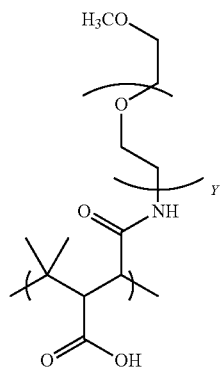

(D')

wherein Y has a value between one and about 100. In some embodiments, Y may have a value between 5 and about 50, such as between 10 and about 20, such as about 12, or about 15.

In some embodiments of the invention, the R group may be functionalized with an amine-reactive fluorescent dye in order to couple the dye to the polymer. Exemplary dyes for coupling to the polymer include Cyanine3 NHS ester, Cyanine5 NHS ester, Cyanine3.5 NHS ester, Cyanine5.5 NHS ester, Alexa Fluor® 488 NHS Ester, and X-Rhodamine-5-(and-6)-Isothiocyanate (5(6)-XRITC).

In some embodiments, the polymer of the present invention may comprise repeat units (A') and (D). A polymer comprising repeat units (A') and (D) may have the following structure:

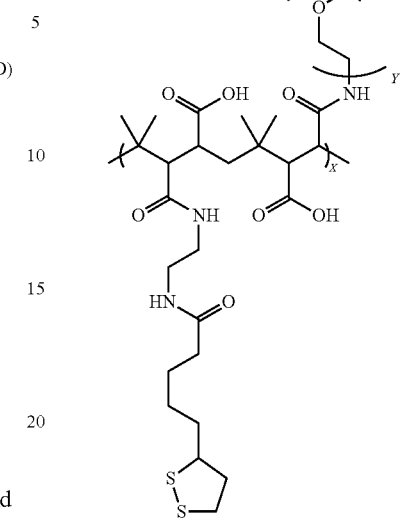

wherein Y has a value between one and about 100, X has a value between about 10 and about 10,000, and each R is independently selected from the group consisting of hydroxyl (—OH), methoxy (—OCH$_3$), amino (—NH$_2$), azido (—N$_3$), thiol (—SH), lipoic acid, ethynyl (—C≡CH), carboxyl (—COOH), aldehyde (—C(O)H), maleimide, and biotin. In some embodiments, Y may have a value between 5 and about 50, such as between 10 and about 20, such as about 12, or about 15. In some embodiments, X may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units.

In some embodiments, the polymer of the present invention may comprise repeat units (A") and (D). A polymer comprising repeat units (A") and (D) may have the following structure:

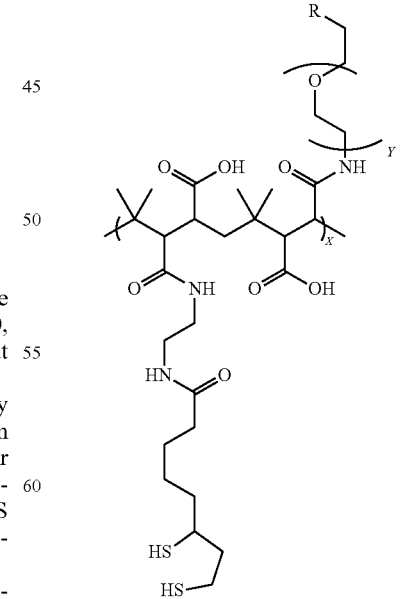

wherein Y has a value between one and about 100, X has a value between about 10 and about 10,000, and each R is independently selected from the group consisting of hydroxyl (—OH), methoxy (—OCH₃), amino (—NH₂), azido (—N₃), thiol (—SH), lipoic acid, ethynyl (—C≡CH), carboxyl (—COOH), aldehyde (—C(O)H), maleimide, and biotin. In some embodiments, Y may have a value between 5 and about 50, such as between 10 and about 20, such as about 12, or about 15. In some embodiments, X may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units.

In some embodiments, the polymer of the present invention may comprise repeat units (B) and (D). A polymer comprising repeat units (B) and (D) may have the following structure:

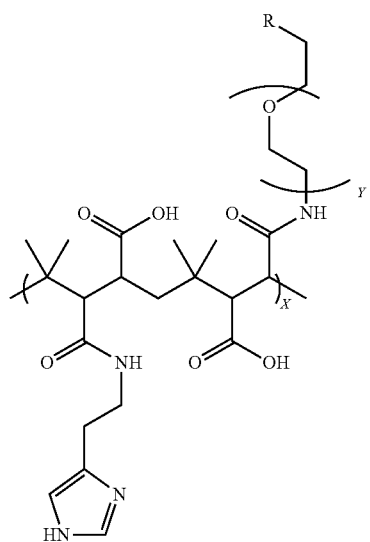

wherein Y has a value between one and about 100, X has a value between about 10 and about 10,000, and each R is independently selected from the group consisting of hydroxyl (—OH), methoxy (—OCH₃), amino (—NH₂), azido (—N₃), thiol (—SH), lipoic acid, ethynyl (—C≡CH), carboxyl (—COOH), aldehyde (—C(O)H), maleimide, and biotin. In some embodiments, Y may have a value between 5 and about 50, such as between 10 and about 20, such as about 12, or about 15. In some embodiments, X may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units.

Polymers of the present invention may comprise repeat units (A'), (A"), (B), (C), (D), and (D') in any combination and any arrangement. The repeat units may be arranged in random, alternating, or block formations. In some embodiments, the polymer of the present invention may comprise repeat units selected from among (A'), (A"), (B), and (D). In some embodiments, the polymer of the present invention may comprise repeat units selected from among (A'), (A"), (B), (D), and (D'). In some embodiments, the polymer of the present invention may comprise repeat units selected from among (A'), (A"), (C) and (D). In some embodiments, the polymer of the present invention may comprise repeat units selected from among (A'), (A"), (C), (D), and (D'). In some embodiments, the polymer of the present invention may comprise repeat units (B), (C), and (D). In some embodiments, the polymer of the present invention may comprise repeat units (B), (C), (D), and (D'). In some embodiments, the polymer of the present invention may comprise repeat units selected from among (A'), (A"), (B), (C), and (D). The molar ratio of amine-containing reactant (i.e., LA and/or DHLA and/or and/or histamine reactant) and poly(ethylene glycol) reactant may be between about 4:1 to about 1:4, such as between about 3:1 to about 1:3, such as between about 2:1 to about 1:2, such as about 1:1.

In some embodiments, the polymer of the present invention may comprise repeat units (A'), (B), and (D). A polymer comprising repeat units (A'), (B), and (D) may have the following structure:

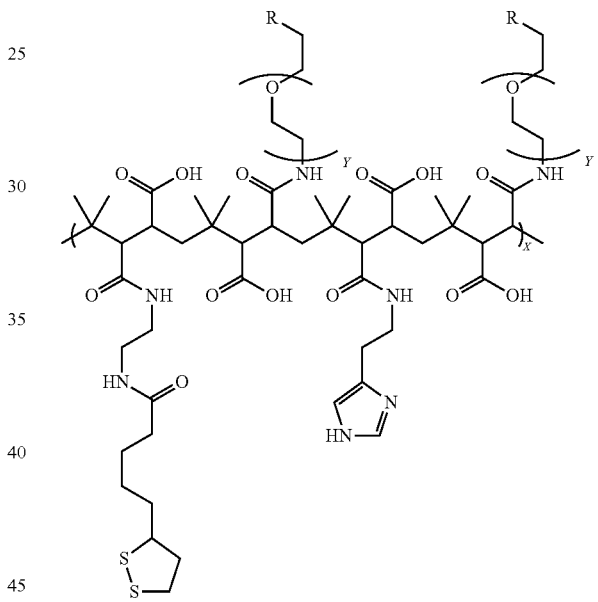

wherein Y has a value between one and about 100, X has a value between about 10 and about 10,000, and each R is independently selected from the group consisting of hydroxyl (—OH), methoxy (—OCH₃), amino (—NH₂), azido (—N₃), thiol (—SH), lipoic acid, ethynyl (—C≡CH), carboxyl (—COOH), aldehyde (—C(O)H), maleimide, and biotin. In some embodiments, Y may have a value between 5 and about 50, such as between 10 and about 20, such as about 12, or about 15. In some embodiments, X may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units.

In some embodiments, the polymer of the present invention may comprise repeat units (A"), (B), and (D). A polymer comprising repeat units (A'), (B), and (D) may have the following structure:

19

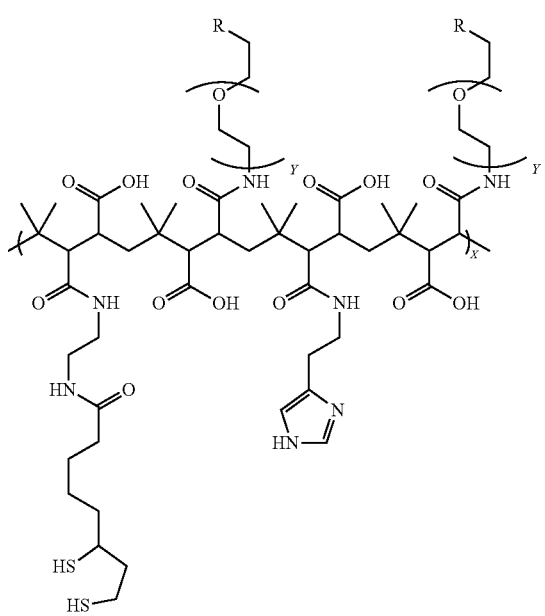

wherein Y has a value between one and about 100, X has a value between about 10 and about 10,000, and each R is independently selected from the group consisting of hydroxyl (—OH), methoxy (—OCH$_3$), amino (—NH$_2$), azido (—N$_3$), thiol (—SH), lipoic acid, ethynyl (—C≡CH), carboxyl (—COOH), aldehyde (—C(O)H), maleimide, and biotin. In some embodiments, Y may have a value between 5 and about 50, such as between 10 and about 20, such as about 12, or about 15. In some embodiments, X may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units.

In some embodiments, the polymer of the present invention may comprise repeat units (A'), (B), and (D'). A polymer comprising repeat units (A'), (B), and (D') may have the following structure:

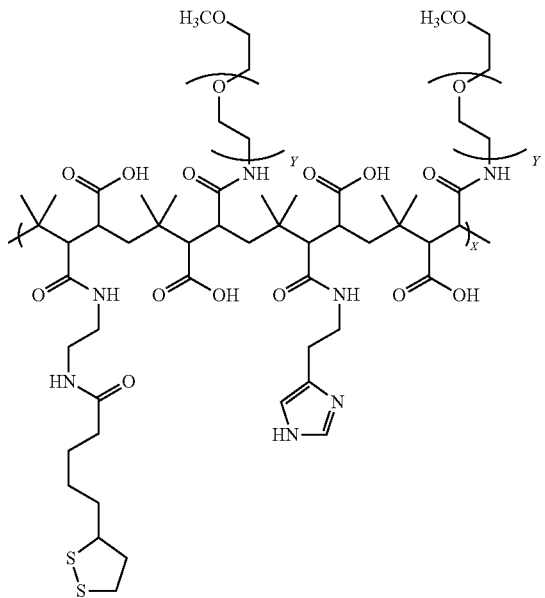

20 wherein Y has a value between one and about 100, X has a value between about 10 and about 10,000. In some embodiments, Y may have a value between 5 and about 50, such as between 10 and about 20, such as about 12, or about 15. In some embodiments, X may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units.

In some embodiments, the polymer of the present invention may comprise repeat units (A"), (B), and (D'). A polymer comprising repeat units (A'), (B), and (D') may have the following structure:

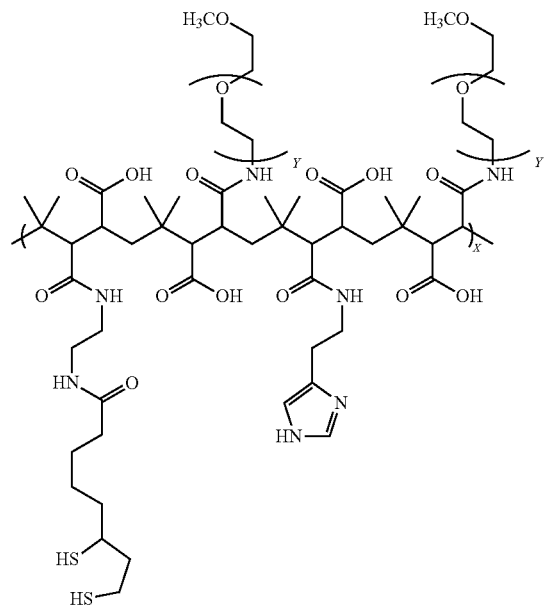

wherein Y has a value between one and about 100, X has a value between about 10 and about 10,000. In some embodiments, Y may have a value between 5 and about 50, such as between 10 and about 20, such as about 12, or about 15. In some embodiments, X may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units.

In some embodiments, the polymer of the present invention may comprise repeat units (A'), (B), (D), and (D'). A polymer comprising repeat units (A'), (B), (D), and (D') may have the following structure:

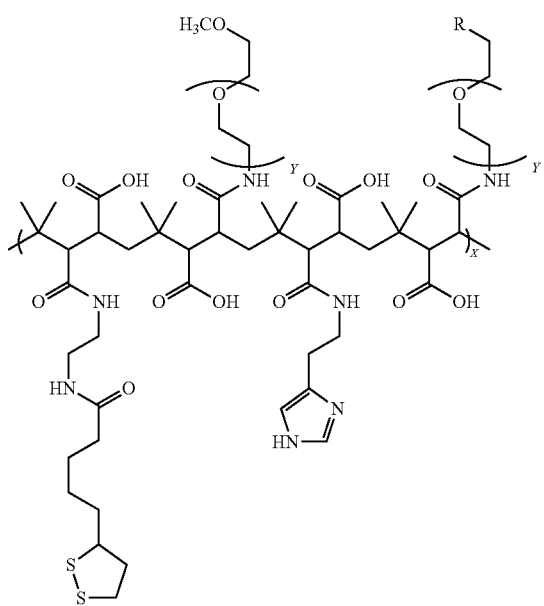

wherein Y has a value between one and about 100, X has a value between about 10 and about 10,000, and each R is independently selected from the group consisting of hydroxyl (—OH), methoxy (—OCH$_3$), amino (—NH$_2$), azido (—N$_3$), thiol (—SH), lipoic acid, ethynyl (—C≡CH), carboxyl (—COOH), aldehyde (—C(O)H), maleimide, and biotin. In some embodiments, Y may have a value between 5 and about 50, such as between 10 and about 20, such as about 12, or about 15. In some embodiments, X may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units.

In some embodiments, the above polymer may be represented as follows:

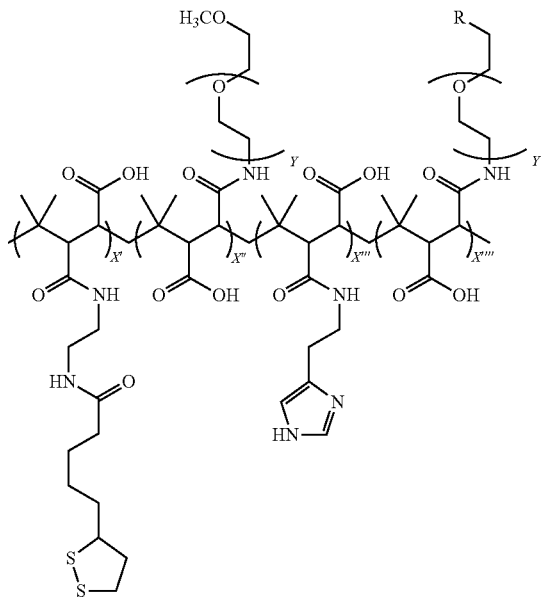

wherein Y has a value between one and about 100, each of X', X", X'", and X"" has a value between about 2 and about 5,000, and each R is independently selected from the group consisting of hydroxyl (—OH), methoxy (—OCH$_3$), amino (—NH$_2$), azido (—N$_3$), thiol (—SH), lipoic acid, ethynyl (—C≡CH), carboxyl (—COOH), aldehyde (—C(O)H), maleimide, and biotin. In some embodiments, Y may have a value between 5 and about 50, such as between 10 and about 20, such as about 12, or about 15. In some embodiments, each of X', X", X'", and X"" has a value between about two and about 1,000, or between about 2 repeat units and about 500 repeat units, such as between about 3 repeat units and about 100 repeat units, between about 4 repeat units and about 50 repeat units, such as between about 4 repeat units and about 20 repeat units. The use of X', X", X'", and X"" is not intended to mean that each of the repeat units are present in block formation. Instead, the use of X', X", X'", and X"" is to provide the range of repeat units in the polymer. The various repeat units may be arranged in alternating, block, or random configurations.

In some embodiments, the polymer of the present invention may comprise repeat units (A"), (B), (D), and (D'). A polymer comprising repeat units (A'), (B), (D), and (D') may have the following structure:

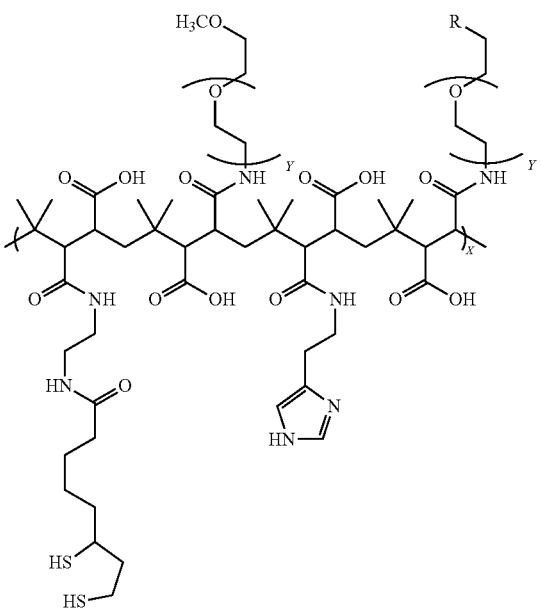

wherein Y has a value between one and about 100, X has a value between about 10 and about 10,000, and each R is independently selected from the group consisting of hydroxyl (—OH), methoxy (—OCH$_3$), amino (—NH$_2$), azido (—N$_3$), thiol (—SH), lipoic acid, ethynyl (—C≡CH), carboxyl (—COOH), aldehyde (—C(O)H), maleimide, and biotin. In some embodiments, Y may have a value between 5 and about 50, such as between 10 and about 20, such as about 12, or about 15. In some embodiments, X may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units.

Contacting PIMA with N-(2-aminoethyl)-4-(1,2-dithiolan-3-yl)pentamide (amine-terminated lipoic acid) and/or N-(2-aminoethyl)-6,8-dimercaptooctanoic acid (amine-terminated DHLA) and/or histamine and/or PEG reactants causes a ring-opening reaction to occur in which the amine-containing reactant is coupled to the maleic anhydride moiety using nucleophilic addition. The contact may occur in an organic, aprotic solvent, such as dimethylformamide, hexane, benzene, toluene, 1,4-dioxane, chloroform, diethyl ether, dichloromethane, tetrahydrofuran, ethyl acetate, acetone, acetonitrile, dimethylsulfoxide, and the like. In general, the nucleophilic coupling reaction may occur at elevated temperatures, such as between about 25° C. and about 200° C., such as between about 35° C. and about 100° C., such as between about 40° C. and about 70° C.

A polymer according to the present invention may have a molecular weight, Mw, between about 1000 Daltons and about 1,000,000 Daltons, such as between about 1000 Daltons and about 500,000 Daltons. In some embodiments, the polymer may comprise between about 10 repeat units and about 20,000 repeat units, such as between about 10 repeat units and about 10,000 repeat units, such as between about 10 repeat units and about 1000 repeat units, or between about 10 repeat units and about 100 repeat units, or between about 20 repeat units and about 50 repeat units.

The nucleophilic addition reaction yields lateral distinct functionalities attached to the chain via amide bonds; it also frees several carboxylic acid groups along the backbone (as many as the number of maleic anhydrides), which provide additional hydrophilicity and potential reactive groups for bioconjugation. The architecture of the final ligand can be optimized by controlling the molar ratio of each amine-modified moiety with respect to the maleic anhydride groups in the PIMA chain. Employing certain embodiments of this platform, we have designed four sets of polymer ligands: LA-PIMA-PEG, His-PIMA-PEG, LA/His-PIMA-PEG, and LA/His-PIMA-PEG-R, where R designates a reactive group, such as amine, azide and biotin; a summary list of the ligands prepared in this study is provided in Table 1.

be adjusted from 30:70 to 50:50, allowing a side-by-side comparison with other ligands. In this work, we focus on the ligand prepared with histamine:PEG-amine molar ratio of 50:50. 3) The third set is made of LA/His-PIMA-PEG, which contains a stoichiometric mixture of 20% LA, 30% histamine and 50% methoxy-PEG per chain. 4) The last set, LA/His-PIMA-PEG-R, is made of a stoichiometric mixture of LA (20%), histamine (30%), methoxy-PEG (45%) and reactive PEG moieties (5%). This is achieved by replacing 5% of methoxy-PEG-amine with R-PEG-amine during the reaction. Here we show one example of amine functionalized polymers, but other reactive ligands can be easily obtained by changing the type of reactive group used (e.g., starting with azide-PEG-amine or biotin-PEG-amine) See References 58 and 59. In particular, if a mixture of different R-PEG-amine moieties (e.g., azide($R_1$)-PEG-amine along with biotin($R_2$)-PEG-amine) is used to prepare the amphiphilic polymer, this can yield hydrophilic QDs that are ideally adapted for orthogonal coupling to target molecules. Additional details about the ligand synthesis and $^1$H NMR characterization are provided in the Examples. Overall the data shown in Table 1 indicate that the molar fractions of the various moieties per PIMA chain (i.e., stoichiometry), extracted from the $^1$H NMR spectra, are consistent with the nominal values of the starting amine-modified molecules used during the addition reaction. For instance, for LA/His-PIMA-PEG we measured multiplet peaks at ~1.1-2.4 ppm and ~3.1 ppm characteristics of the lipoic acid protons, two peaks at ~6.8 and ~7.6 ppm ascribed to the protons of the imidazole ring, along with a strong peak at ~3.5 ppm and a sharp peak at ~3.2 ppm attributed to the PEG and terminal methoxy protons, respectively. A broad peak at ~0.9 ppm ascribed to the methyl protons of the polymer backbone was also measured. The degree of grafting was estimated by comparing the integration ratio of $^1$H NMR peaks of LA (2H, δ ~2.1 ppm), His (1H, δ ~6.8 ppm), methoxy group

TABLE 1

Summary of the prepared ligands, along with the nominal and experimentally estimated numbers of coordinating groups and PEG moieties per PIMA chain for each compound.

| Ligand | (Molar Fraction) | Nominal Numbers per Chain[a] | Experimental Numbers per Chain[b] |
|---|---|---|---|
| LA-PIMA-PEG | LA:PEG 30:70 | LA: 12 PEG: 27 | LA: 13 PEG: 27 |
| His-PIMA-PEG | His:PEG 30:70 | His: 12 PEG: 27 | His: 10 PEG: 27 |
| His-PIMA-PEG | His:PEG 50:50 | His: 20 PEG: 20 | His: 17 PEG: 19 |
| LA/His-PIMA-PEG | LA:His:PEG 20:30:50 | LA: 8 His: 12 PEG: 20 | LA: 10 His: 12 PEG: 18 |
| LA/His-PIMA-PEG-R | LA:His:PEG:PEG-R 20:30:45:5 | LA: 8 His: 12 PEG: 18 R: 2 | |

[a]The reported values for the various moieties were obtained from the starting molar concentrations of the amine-modified molecules (e.g., lipoic acid-amine (x), histamine (y), PEG-amine (z) and R-PEG-amine (z')) in comparison to that of the maleic anhydride groups of the PIMA.
[b]The values were obtained by comparing the $^1$H NMR peak integration of the LA (δ~2.1 ppm), His (δ~6.8 ppm), PEG (δ~3.2 ppm) to the methyl groups of PIMA (~234 H, δ~0.8-1.0 ppm).

1) The first set, LA-PIMA-PEG, is prepared by reacting PIMA with a mixture of 30% lipoic acid-amine and 70% methoxy-PEG-amine. Here the molar fraction of maleic anhydrides reacted with LA-NH$_2$ is maintained at 30% or smaller, in order to avoid issues of insolubility encountered in reference 35 (with polyacrylic acid precursor), although higher fractions of lipoic acid can be introduced using the current synthetic route. 2) The second set is made of His-PIMA-PEG. The synthesis is similar to that of LA-PIMA-PEG, but the lipoic acid-amine is replaced with histamine. The molar ratio of histamine:PEG-amine could (3H, δ ~3.2 ppm) to the two methyl repeat units in a PIMA chain (~234H, δ ~0.9 ppm). We deduced that ~10 lipoic acid groups (21.0H), ~12 histamines (12.4H) and ~18 methoxy groups (54.0H, i.e., 18 PEG moieties) were introduced per chain.

II. Ligand Exchange and Phase Transfer.

In some embodiments, the invention provides a composition comprising a core nanoparticle material coated with a polymer ligand according to the present invention. A nanoparticle is generally a spherically shaped material having a diameter generally between about 1 nanometer and about 10,000 nanometers in diameter, such as between about 1 nanometer and about 2500 nanometers in diameter, or between about 1 nanometer and about 1000 nanometers in diameter, or between about 1 nanometer and about 100 nanometers in diameter. In some embodiments, the nanoparticle comprises a magnetic material. In some embodiments, the nanoparticle comprises a non-magnetic material. In some embodiments, the nanoparticle comprises a material selected from the group consisting of $Fe_3O_4$, $Fe_2O_3$, FePt, Co, Mn-doped $Fe_3O_4$, CdSeS/ZnS, InP/ZnS, PbS, CdTe, CoPt, FeCoPt, $CoFe_2O_4$, MnO, $Mn_3O_4$, $Co_3O_4$, FeO, Ni, $TiO_2$, $Al_2O_3$, CdSe, PbSe, $ZrO_2$, ZnO, Au, Ag, and graphene oxide.

According to the present invention, nanoparticles may be capped or enclosed in a shell structure comprising the polymer of the present invention. Capping or enclosing the nanoparticle may occur by contacting a nanoparticle with a polymer of the present invention. In some embodiments, the polymer ligand of the present invention may displace an organic molecule, such as an oleic acid, that caps or encloses the nanoparticle. The organic molecule which caps the nanoparticle is often hydrophobic, and the nanoparticle may be dispersed in a hydrophobic solvent. By carrying out a ligand exchange reaction, the polymer of the present invention may convert a hydrophobic particle into a hydrophilic particle.

In some embodiments, ligand exchange of CdSe—ZnS QDs with LA-containing ligands is carried out under borohydride-free conditions using a novel and mild photoligation strategy. See Reference 60. We have previously shown that such strategy is applicable to an array of LA-based small molecules, including LA-PEG-OMe, LA-PEG-COOH/$NH_2$, and bis(LA)-zwitterion. See References 34 and 60. Here, we expand this strategy to polymer ligands, namely LA-PIMA-PEG, LA/His-PIMA-PEG and LA/His-PIMA-PEG-$NH_2$.

The effectiveness of the photoligation strategy applied to LA-based ligands stems from the photochemical sensitivity of the strained dithiolane ring to UV excitation. Indeed, LA exhibits a well-defined absorption peak at ~340 nm. This absorption peak continuously decreases with time to nearly background level after ~20-30 min of UV irradiation at 350 nm; such change has been attributed to the photochemical transformation of the dithiolane to several products including dithiol groups and dithiol radicals. See References 60 and 61. Here too, we found that UV irradiation of LA-PIMA-PEG yields similar change in the optical feature of the dithiolane ring, though this change is less pronounced due to rather strong background contribution from the polymer to the absorption spectrum. In the case of LA/His-PIMA-PEG, a slightly shorter irradiation time (~10 min) was needed, presumably due to the smaller number of lipoic acid groups per PIMA chain compared with LA-PIMA-PEG. It is worth noting that following irradiation of the LA/His-PIMA-PEG ligand, the measured absorption profile is essentially identical to that collected from pure His-PIMA-PEG, indicating that the imidazole groups do not exhibit a photochemical response. We further verified that the absorption feature and $^1$H NMR characteristic peaks of His-PIMA-PEG are not altered by UV irradiation.

The photoligation of QDs with LA-PIMA-PEG was performed using one phase configuration, where hydrophobic QDs and ligands were dispersed in THF followed by the addition of a small amount of tetramethylammonium hydroxide catalyst pre-dissolved in methanol. The mixture was irradiated for 20 min while stirring using a UV reactor, followed by precipitation with excess hexane. After evaporation of the residual solvent under vacuum, the QDs were readily dispersed in DI water. For LA/His-PIMA-PEG or LA/His-PIMA-PEG-R, ligand exchange was carried out using a slightly modified procedure. The mixture of hydrophobic QDs and ligands in THF were first stirred for 2 hours prior to UV irradiation. This allowed for imidazole coordination onto the QD surfaces. In this case the photoirradiation can be applied to the LA groups along the ligated polymer in either organic solvent, or even aqueous media (if the QDs were transferred to water after 2-hour reaction in THF). Cap exchange with His-PIMA-PEG was carried out by mixing the hydrophobic QDs and His-PIMA-PEG ligands in THF and stirring the mixture for 2 hours at 40° C., followed by purification. These procedures yielded QDs that were readily dispersed in water.

III. Characterization of the Hydrophilic QDs.

The hydrophilic QD dispersions have been characterized using three complementary analytical techniques: 1) absorption and fluorescence spectroscopy; 2) dynamic light scattering; 3)$^1$H NMR spectroscopy. $^1$H NMR was further utilized to estimate the surface ligand density.

1) Optical Characterization.

Figure 1B:
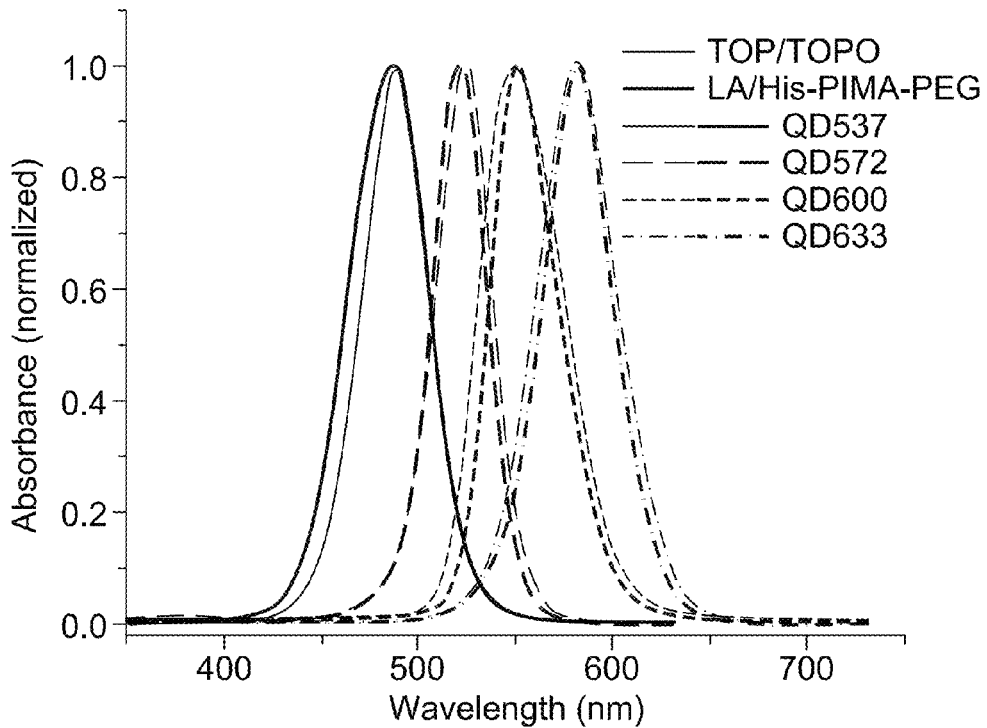
FIG. 1B is an emission spectra of four representative QDs emitting at, from left to right, 537, 572, 600 and 633 nm, before and after photoligation with LA/His-PIMA-PEG ligands.

FIGS. 1A and 1B show absorption and emission spectra of 4 representative sets of QDs emitting at, from left to right, 537, 572, 600 and 633 nm, respectively, before and after photoligation with LA/His-PIMA-PEG ligands. The spectral properties of the QDs capped with LA/His-PIMA-PEG are essentially identical to those measured for hydrophobic nanocrystals dispersed in hexane. Similar data were collected for QDs ligated with His-PIMA-PEG and LA-PIMA-PEG. However, a slight red shift (~1-5 nm) in absorption and emission peaks was measured for QDs photoligated with LA-PIMA-PEG, a result consistent with previous findings combining photoligation and LA-PEG-based ligands. See Reference 60. Overall the ligand exchange was rapid and yielded aqueous QD dispersions that exhibited strong fluorescence under UV light.

Influence of the Photoligation on the QD Emission Properties.

Figure 2:
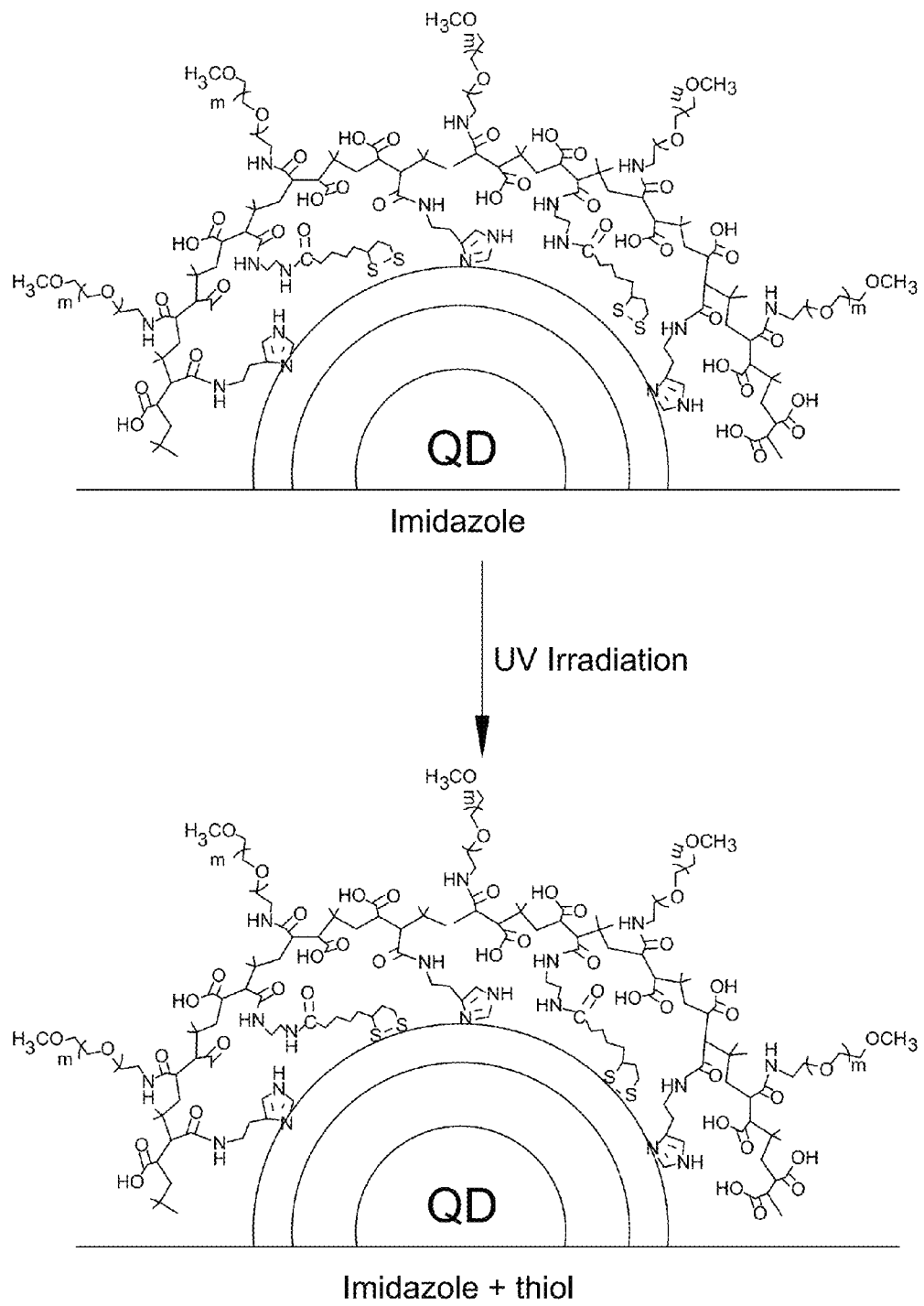
FIG. 2 is an illustration depicting the selective binding of LA anchors on the QDs before and after UV irradiation.

We investigated the effects of combining mixed anchors (LA and His) with photoligation on the emission properties of the resulting water-soluble QDs. For this we conducted ligand exchange of TOP/TOPO-QDs with LA/His-PIMA-PEG in two steps. First, ligand exchange was carried without involving UV-irradiation and the PL spectrum was collected. Here, we anticipate that only the imidazole groups coordinate on the QD surface, leaving the LA groups (in the form of dithiolanes) unattached, because the oxidized groups do not coordinate on the QD surface. See the illustration in FIG. 2. In the next step UV irradiation was applied to the QD dispersion in buffer for 10 min, to allow ligation of the photochemically transformed dithiol groups onto the QD surfaces. Photoligated QDs exhibit a stronger fluorescence, i.e. an enhancement of ~2 is measured. This brightening may be attributed to a combination of: 1) the synergistic effect of two anchoring groups (instead of one) which reduces the ligand desorption and improves the colloidal stability; and 2) the benefit of imidazole coordination on the QD radiative photoluminescence as previously reported. See Reference 48. Additional contribution may emanate from UV promoted photo-annealing of QDs, which can lead to enhancement of photoluminescence by reducing the number of surface trap states. See References 42 and 62-65. Indeed, such photo-induced enhancement in the PL was also observed for His-PIMA-PEG-QDs following irradiation for 10 min in the UV reactor, though the measured enhancement was smaller.

We finally compared the photoluminescence intensities measured from dispersions of QDs ligated with different polymer ligands in buffer (pH 7.5) with that measured from TOP/TOPO-QDs in hexane; the optical densities were maintained identical for all samples. We found that QDs photoligated with LA/His-PIMA-PEG yielded the highest PL, with intensity comparable to that measured from a dispersion of TOP/TOPO-QDs. In comparison, the PL measured from dispersions of QDs ligated with LA-PIMA-PEG or His-PIMA-PEG were slightly lower, with respective intensities equal to ~75% and 76% of that measured for TOP/TOPO-QDs in hexane.

2) Dynamic Light Scattering Measurements.

Figure 3A:
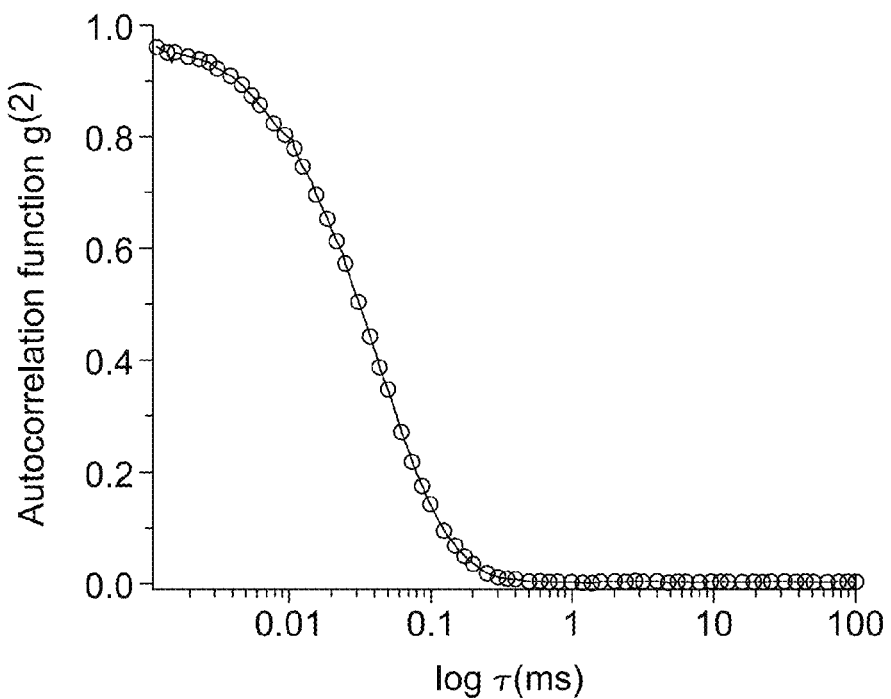
FIG. 3A is a representative plot of the autocorrelation function, $(g^{(2)})$ vs. log (lag time, t), collected from a dispersion of QDs (emission at 537 nm) photoligated with LA/His-PIMA-PEG.

The hydrodynamic sizes were obtained from multi-angle dynamic light scattering (DLS) measurements applied to three sets of QD dispersions (emission at 537 nm) ligated with LA-PIMA-PEG, His-PIMA-PEG, LA/His-PIMA-PEG, dispersed in DI water (pH~6.5). FIG. 3A shows a representative plot of the intensity autocorrelation function, $g^{(2)}$ versus lag (time), collected from the LA/His-PIMA-PEG-QD dispersions in water at a scattering angle $\theta=90°$. Additional plots for $g^{(2)}$, collected using various $\theta$ values (ranging from 60° to 150°), consistently showed that faster decay rates were measured for higher scattering angles as expected (data not shown). Furthermore, a linear dependence of the decay rate versus the square of the scattering wavevector was extracted from the data. See Reference 66. Similar data were collected for the other two sets of QD dispersions. These profiles exhibit faster decays in comparison to those measured for iron oxide and gold nanoparticles, indicating faster diffusion coefficients for smaller size nanocrystals. See References 59 and 67. The corresponding histograms for the intensity vs. hydrodynamic size, extracted from the Laplace transform of the autocorrelation function, along with the polydispersity index (PDI) values are shown in Table 2. The hydrodynamic radii extracted from these measurements are: ~10.9 nm for LA/His-PIMA-PEG-QDs, ~10.3 nm for His-PIMA-PEG-QDs, and ~11.3 nm for LA-PIMA-PEG-QDs. These are only ~2-3 nm larger than what was reported for DHLA-PEG$_{750}$-OCH$_3$-capped QDs. See Reference 66. This compact size reflects the nature of the multi-coordinating ligands, yielding homogeneous QDs with a thin polymer coating.

TABLE 2

Hydrodynamic radius ($R_H$) values and polydispersity index (PDI) measured for 537 nm-emitting QDs ligated with: LA-PIMA-PEG, His-PIMA-PEG, LA/His-PIMA-PEG and DHLA-PEG$_{750}$ (control).

| Capping Ligand | $R_h$ (nm) | PDI |
|---|---|---|
| LA-PIMA-PEG | ~11.3 | 0.14 |
| His-PIMA-PEG | ~10.3 | 0.10 |
| LA/His-PIMA-PEG | ~10.9 | 0.12 |
| DHLA-PEG$_{600}$ | ~7-8 | |

3) $^1$H NMR Characterization.

The dispersion of QDs ligated with LA/His-PIMA-PEG (in D$_2$O) was further characterized using pulsed field gradient-based water suppression $^1$H NMR spectroscopy. $^1$H NMR spectrum collected from a dispersion of QDs photoligated with LA/His-PIMA-PEG show the two resonances at 6.96 and 7.19 ppm, characteristic of protons in the imidazole ring, are weaker and slightly shifted with respect to the peaks measured for the ligand alone. Such shift is attributed to binding of the imidazole to the QD and a change in its environment. The spectrum also shows that the NMR signatures of the TOP/TOPO/HPA measured for the native hydrophobic QDs (e.g., peaks at 0.82 ppm and 1.23 ppm) are conspicuously absent. These results combined clearly indicate that ligation of the QDs and their transfer to buffer media involved removal of the TOP/TOPO/HPA and ligation of LA/His-PIMA-PEG onto the QD surfaces, driven by coordination of imidazole and photochemically-modified LA groups.

We further used $^1$H NMR measurements to extract an estimate for the average number of LA/His-PIMA-PEG per QD, by comparing the molar concentrations of the ligand and QDs following phase transfer and removal of excess unbound ligands. The molar amount of the LA/His-PIMA-PEG was estimated by comparing the integrations of the methyl-protons on the PIMA backbone and the $\alpha$-proton of the pyridine standard, while the concentration of QDs was estimated from the optical absorption at 350 nm. Such analysis indicates that for a ~3 nm radius QDs (core-plus-shell size extracted from TEM and small angle x-ray scattering), with emission peak at 537 nm, there are about 14.5 polymer ligands, which corresponds to ~290 anchors (histamine plus DHLA) and ~261 PEG moieties per nanocrystal. When such analysis is applied to QDs ligated with LA/His-PIMA-PEG-NH$_2$ (5% amine), we roughly estimate that there are ~28 amine groups per nanocrystal. Though these values constitute only approximate estimates for the number of ligands, the resulting number of PEG moieties is comparable to those reported for LA-PEG-coated Au nanoparticles. See Reference 69.

IV. Colloidal Stability Tests.

We have tested the stability of three representative sets of QDs, one set photoligated with LA/His-PIMA-PEG, one photoligated with LA-PIMA-PEG, and one capped with His-PIMA-PEG. Tests focused on several biologically-relevant conditions, including: (1) the pH 3-13 range, (2) in high ionic strength buffer (1 M NaCl), (3) in the presence of competing reducing molecules (0.5 M dithiothreitol, DTT), (4) in 100% cell growth media (RPMI-1640 Medium), and (5) storage at low concentration (10 nM) at 4° C. in the dark and under room temperature with light exposure conditions.

Three sets of green-emitting QD dispersions (0.5 µM) were stability tested over the pH range from 3 to 13, as prepared and after different storage periods extending to 1.5 years. Stability was tested by measuring fluorescence emission over time. Data show that QDs photoligated with LA/His-PIMA-PEG remained stable over the full pH range, with no sign of aggregate build up or loss in fluorescence. In comparison, the dispersions of QDs either ligand exchanged with His-PIMA-PEG or photoligated with LA-PIMA-PEG were stable over the pH range 5-13. However, dispersions at pH 3 though remaining colloidally stable exhibited a progressive and substantial loss in emission after ~8 months for LA-PIMA-PEG-QDs; a more pronounced loss was observed after ~1 month for His-PIMA-PEG-QDs. Dispersions of LA-PIMA-PEG-QDs were less fluorescent than the other two samples over storage period, a property attributed to the nature of the thiol-coordination.

Three sets of QD dispersions were measured for PL intensity progression with storage time for QD dispersions (0.3 µM) in DI water (pH~6.5), and in buffers at pH 3, at pH 7 and at pH 11. The data indicate that under neutral and basic conditions, the PL intensity remained essentially constant. In comparison, only dispersions of LA/His-PIMA-PEG-QDs maintained both colloidal stability and high emission at pH 3 over the full test period. The PL and colloidal stability of His-PIMA-PEG-QDs and LA-PIMA-PEG-QDs was weaker, though losses were much more pronounced for His-PIMA-PEG-capped QDs. For example, after 45 days of storage at pH 3, the PL intensities of the LA-PIMA-PEG- and His-PIMA-PEG-QDs respectively decayed to ~47% and ~16% (compared to freshly prepared samples).

The polymer-ligated QDs were subjected to colloidal stability tests in high ionic strength solutions and in the presence of strong reducing agent (dithiothreitol, DTT). All three sets of QD dispersions stayed stable and aggregate-free for at least 12 months of storage in the presence of 1M NaCl, though a slight loss in the PL signal was observed for nanocrystals capped with His-PIMA-PEG after 8 months. Dispersions of QDs ligated with the three sets of polymer ligands in buffer containing 0.5 M DTT remained homogeneous and highly fluorescent for at least 6 months. Similarly, QDs in 100% cell growth media (RPMI-1640) were characterized by great colloidal stability for at least 2 months, though a slight loss in emission was observed for His-PIMA-PEG-QDs. These results are very promising as they indicate the ability of the present coating to impart colloidal stability, while preventing adsorption of proteins and aggregation in biological media. For instance, DTT is a dithiol derivative that can strongly interact with various metal surfaces and effectively compete for binding with an array of small ligands (e.g., DHLA-PEG), promoting aggregation build of metal nanoparticles in buffer media. See References 37 and 70. The ability of the newly designed metal-coordinating polymers to impart longer term stability to the QDs in 0.5 M DTT is remarkable and bodes well for use in live cell imaging and sensing.

The final test probed the stability of QD dispersions prepared at very low concentrations (10 nM). Fluorescence emission showed that all three sets of QD dispersions stayed fluorescent and homogenous for at least 10 weeks when stored at 4° C., albeit with a slight decrease in the solution brightness. These dispersions also exhibited great colloidal stability when stored under ambient conditions (room temperature with light exposure) for 10 weeks. Nonetheless, we found that QDs ligated with LA-PIMA-PEG exhibited a slightly higher reduction in the solution brightness compared to the other two samples, a property attributable to potential photo-oxidation of the thiol groups in the ligands.

Overall the above data confirm the benefits of combining multiple lipoic acid and imidazole groups along with several PEG moieties within the same amphiphilic ligand. Indeed, combing LA and imidazole in the same macromolecule greatly improves the ligand-to-QD binding while maintaining high fluorescence signal in buffer media compared to ligands (polymeric or molecular scale) presenting thiols or imidazoles only anchors. For instance, the fluorescence of His-PIMA-PEG-QDs and LA-PIMA-PEG-QDs exhibited reduction in the PL emission at pH 3, and/or in growth media and ambient conditions. In comparison, dispersions of LA/His-PIMA-PEG-QDs performed better across the various conditions tested. Our data also indicate that QDs capped with $His_{50\%}$-PIMA-$PEG_{50\%}$ exhibit great colloidal stability and high fluorescence at pH 5 (acidic conditions), even though the pKa of imidazole is ~6. The ligands with lower imidazole coordinating groups (e.g., $His_{30\%}$-PIMA-$PEG_{70\%}$-QDs) provide weaker colloidal stability at pH 5 (see FIG. S10), consistent with previous report. See Reference 44. These findings combined clearly reflect the benefits of high coordination afforded by the polymer ligand compared to those presenting lower coordination numbers.

V. Further Functionalization of the Polymer-Coated QDs.

Introduction of reactive groups into the polymer structure allows further coupling to specific molecules (e.g., dyes and peptides). As such we have explored activation of amine on QDs photoligated with LA/His-PIMA-PEG-$NH_2$ with two distinct functionalities, along with activation of carboxylic groups available on QDs ligated with LA/His-PIMA-PEG-$OCH_3$: 1) Coupling to Cy3 dye to test energy transfer interactions; 2) Coupling to the neurotransmitter dopamine to provide a pH-sensitive fluorescent platform where emission is controlled by pH-controlled charge transfer interactions. 3) EDC/NHS-driven modification of the carboxylic groups along the polymer backbone, freed during the ligand synthesis, with cell penetrating peptides (CPP) to form QD-CPP conjugates and promote intracellular uptake and imaging.

1. Covalent Conjugation to FRET Dyes.

Figure 4A:
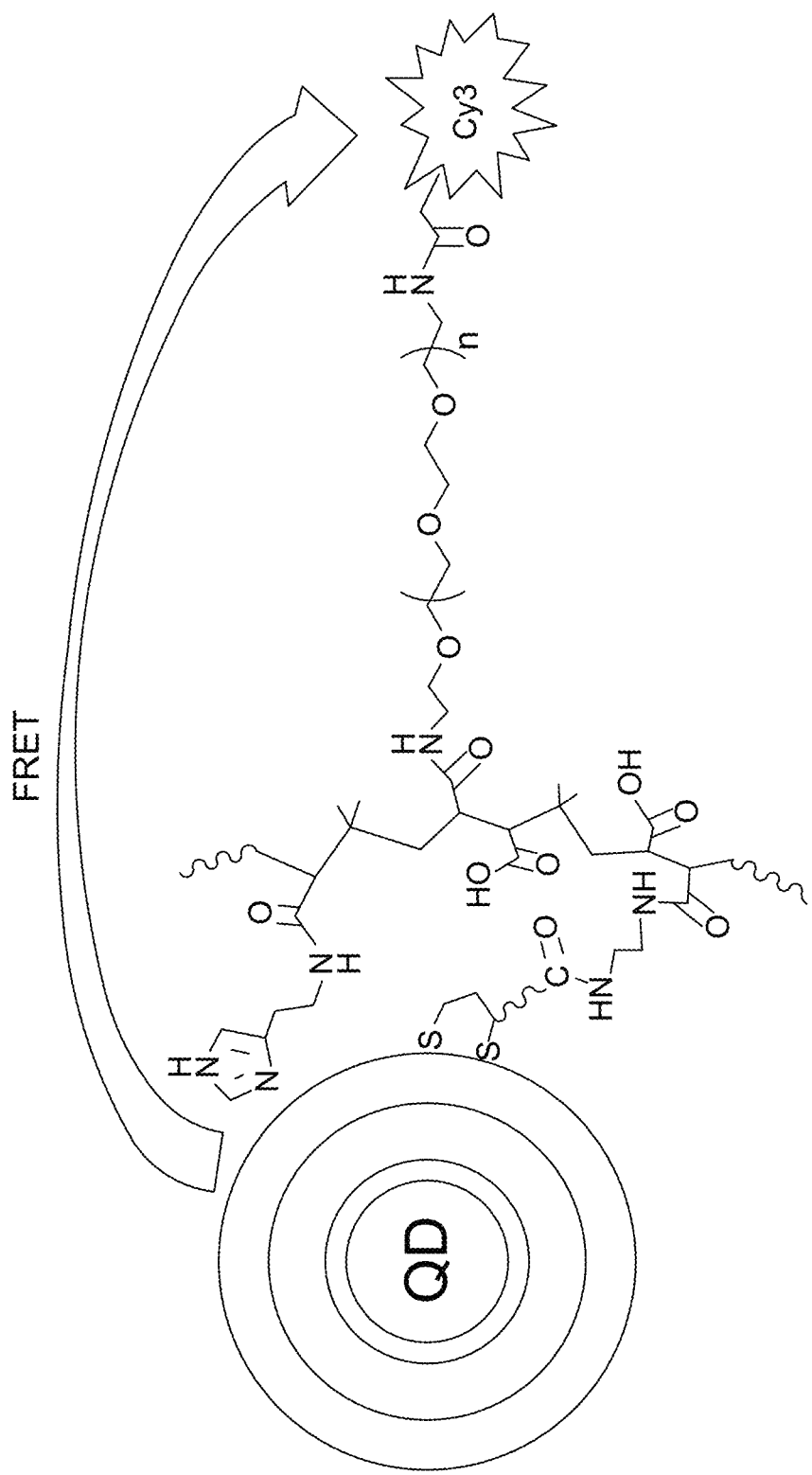
FIG. 4A is a schematic representation of the covalent conjugation of sulfo-Cy3 NHS-ester dye to amine-functionalized QDs.
Figure 4B:
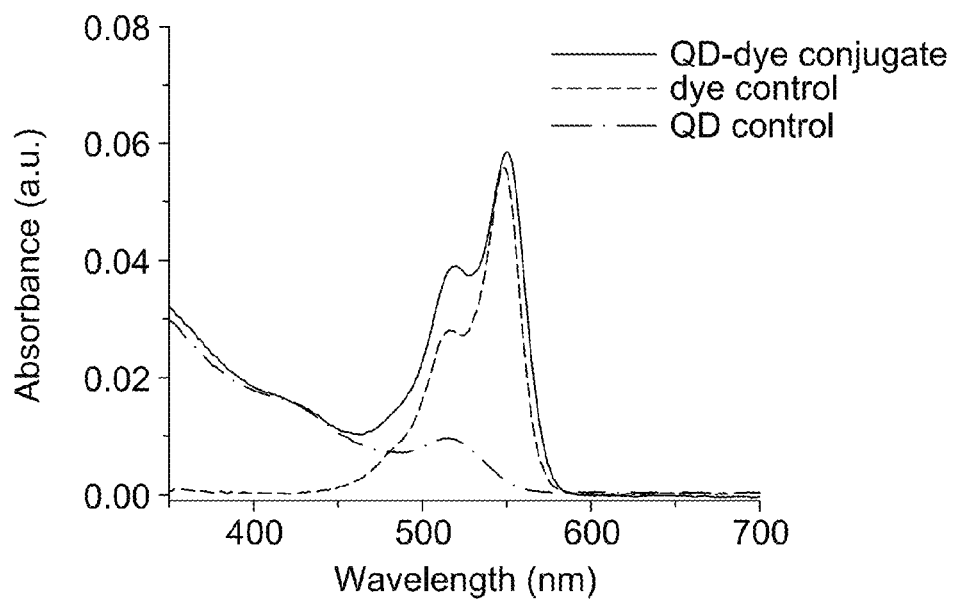
FIG. 4B is an Absorption spectra collected from: purified QD-dye conjugates (solid line, -), pure QDs (broken line with intervening dots, - • - • -) and pure dye (broken line, - - -) in water.
Figure 4C:
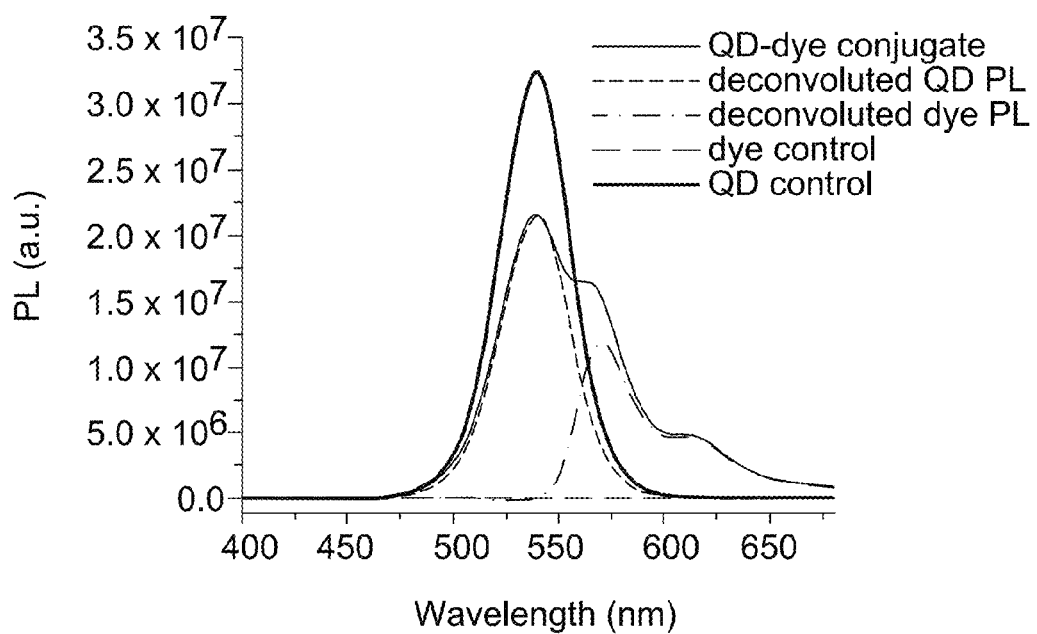
FIG. 4C is a composite emission spectrum of QD-dye conjugates (solid line, -), pure dye (broken line, - - -), and pure QDs (thick, solid line —) together with the deconvoluted contributions of the QDs (broken line, - - -) and dye (broken line with intervening dots, - • - • -). The fluorescence spectra were generated using 350 nm excitation.

Amine-functionalized nanocrystals (QDs photoligated with LA/His-PIMA-PEG-amine) were reacted with NHS-ester modified sulfo-Cy3 following conventional protocol. See FIGS. 4A through 4C and Reference 58. FIG. 4A is a schematic representation of the covalent conjugation of sulfo-Cy3 NHS-ester dye to amine-functionalized QDs. FIG. 4B is an Absorption spectra collected from: purified QD-dye conjugates (solid line, -), pure QDs (broken line with intervening dots, - • - • -) and pure dye (broken line, - - -) in water. FIG. 4C is a composite emission spectrum of QD-dye conjugates (solid line, -), pure dye (broken line, - - -), and pure QDs (thick, solid line ▬) together with the deconvoluted contributions of the QDs (broken line, - - -) and dye (broken line with intervening dots, - • - • -). The fluorescence spectra were generated using 350 nm excitation. After removal of excess unreacted dye and byproducts, the absorption and PL spectra were collected. The data shown in FIGS. 4B and 4C indicate that the absorption spectrum collected from the conjugates is a composite of QD and Cy3 dye contributions. Furthermore, deconvolution of the composite photoluminescence spectrum (using 350 nm excitation) shows a sizable decrease in the QD fluorescence along with an increase of the dye contribution; in comparison a negligible direct excitation contribution is measured from a control Cy3 alone. Following deconvolution of the absorption spectra of the conjugates and using the extinction coefficient of the dye and QD, we estimate that the average number of conjugated Cy3 per QD is equal to 2.8 (~3). The FRET efficiency calculated using the relation:

$$E=1-F_{DA}/F_D,$$

where $F_{DA}$ and $F_D$ designate the PL intensity measured for QD-Cy3 conjugates and QDs alone, is 33.4%. Comparison to the FRET efficiency extracted from the Förster dipole-dipole model using the experimental spectral overlap integral indicates that the center-to-center separation distance is about 61 Å, which further proved that the polymer coating developed here provides a rather compact coating of the QD.

2. Coupling to Dopamine Yields a pH-Controlled QD Photoluminescence.

Figure 5A:
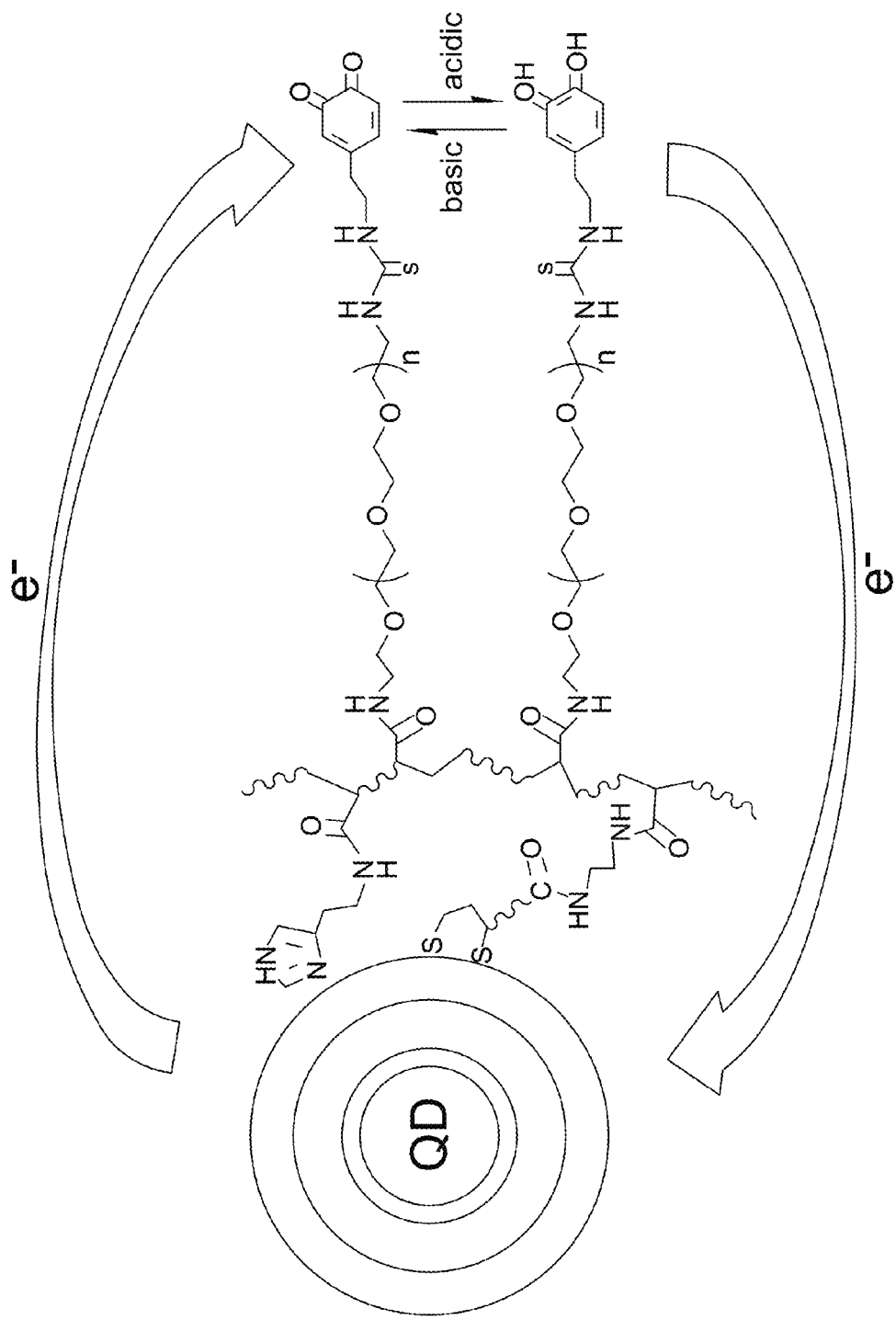
FIG. 5A is a schematic of the assembly of dopamine-ITC onto amine-functionalized QDs via isothiourea bond.
Figure 5B:
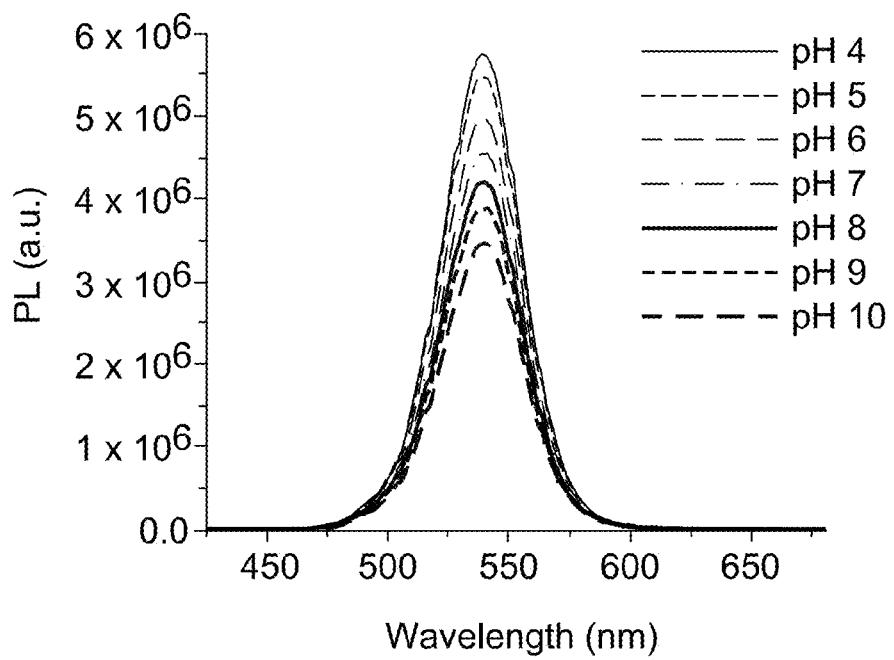
FIG. 5B are steady-state fluorescence spectra collected from solutions of QD-dopamine conjugates in buffers ranging from pH 4 to 10.
Figure 5C:
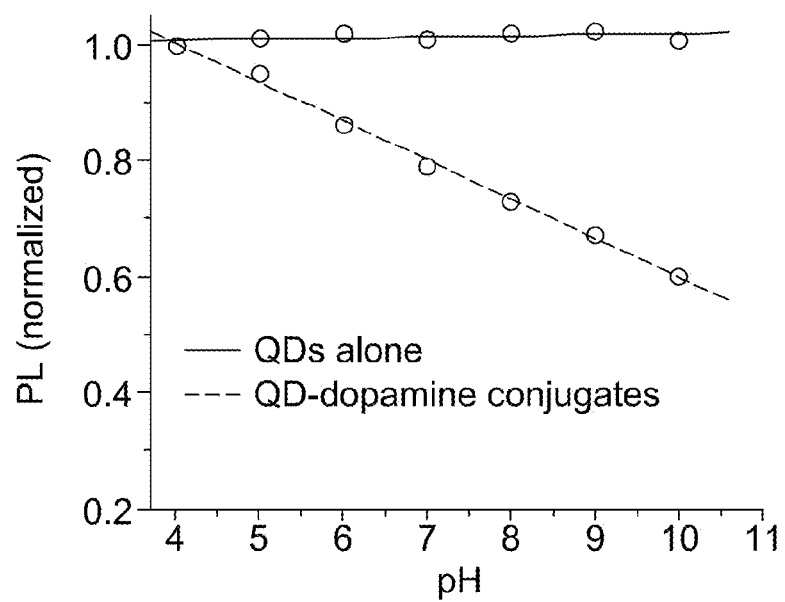
FIG. 5C is the corresponding integrated PL intensities normalized with respect to the value at pH 4 (broken line with downward slope). The PL intensity of QDs alone was insensitive to pH changing (solid line).

We further tested the reactivity of the QDs ligated with LA/His-PIMA-PEG-$NH_2$ by reacting them with dopamine-isothiocyanate, which yields QD-dopamine conjugates via a covalent isothiourea bond. See FIGS. 5A through 5C and Reference 24. FIG. 5A is a schematic of the assembly of dopamine-ITC onto amine-functionalized QDs via isothiourea bond. FIG. 5B are steady-state fluorescence spectra collected from solutions of QD-dopamine conjugates in buffers ranging from pH 4 to 10. FIG. 5C is the corresponding integrated PL intensities normalized with respect to the value at pH 4 (broken line with downward slope). The PL intensity of QDs alone was insensitive to pH changing (solid line). After removal of the excess unreacted dopamine-ITC, we tracked the changes in the PL collected from QD-dopamine conjugates using steady-state and time-resolved fluorescence measurements when the pH of the buffer was progressively switched from acidic to alkaline. FIG. 5B shows that the PL spectra collected from dispersions of these conjugates changed with increasing pH, as reported for other QD-dopamine conjugates. The above PL loss was coupled with a progressive shortening in the QD PL lifetime when the solution pH was changed. Cumulative plots for the relative changes in PL with the solution pH show a decrease in the PL intensity with increasing solution pH. In comparison, there were no measurable changes in the PL for control dispersions made of polymer-coated QDs but without coupled dopamine. The progressive loss in QD PL with increasing pH is attributed to the pH-dependent chemical transformation of dopamine: namely a decrease in the oxidation potential of the catechol (reduced form) combined with increased concentration of quinone (oxidized form) when the pH of the buffer is increased, as schematically illustrated in FIG. 5C. Both transformations promote a pH-dependent enhancement in the charge transfer interactions for the QD-dopamine conjugates, manifesting in a progressive and pronounced quenching of the QD PL with increasing pH.

3. Intracellular Uptake of QD-CPP Conjugates and Cytotoxicity Tests.

Figure 6A:
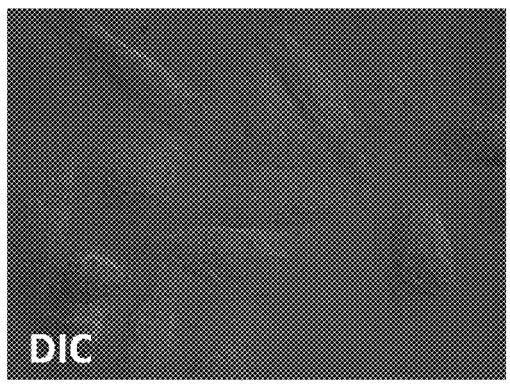
FIGS. 6A through 6D are representative epifluorescence images of HeLa cells incubated with QD-CPP conjugates at 200 nM for 1 hour. Images correspond to the differential interference contrast (FIG. 6A, DIC), DAPI emission (FIG. 6B, which is blue), QD emission at 537 nm (FIG. 6C, which is green), and the merged images (FIG. 6D).
Figure 6B:
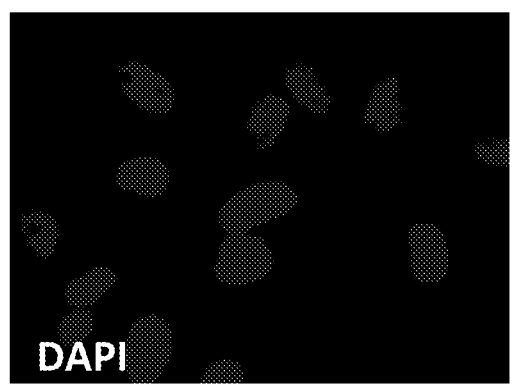
Figure 6C:
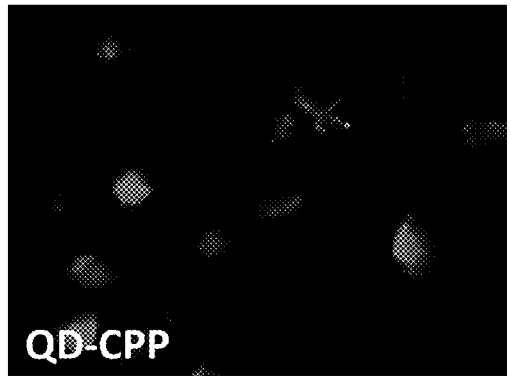
Figure 6D:

Here we started with LA/His-PIMA-PEG-OCH$_3$-capped QDs which were further coupled to cell penetrating peptides (CPP) via EDC/NHS chemistry. The carboxylic acid groups freed along the PIMA backbone were activated with EDC/NHS, and then amine-terminated CPP were added to promote carboxyl-to-amine crosslinking. Following purification using a PD10 column, the conjugates were tested for their ability to promote intracellular uptake. We estimated that there were ~5 CPP per QD-conjugate, assuming 100% reaction efficiency when starting with a CPP:QD molar ratio of 5:1. FIG. 6A through 6D are a representative set of fluorescence images collected for HeLa cells incubated with QD-CPP conjugates at 200 nM for 1 hour together with one collected from culture incubated with unconjugated QDs. Representative epifluorescence images of HeLa cells incubated with QD-CPP conjugates at 200 nM for 1 hour. Images correspond to the differential interference contrast (DIC, FIG. 6A), DAPI emission (FIG. 6B, which is blue), QD emission at 537 nm (FIG. 6C, which is green), and the merged images (FIG. 6D). The images show that the QD green signal was observed only for cells incubated with the QD-CPP conjugates, and no intracellular QD fluorescence was detected for the cells incubated with the same concentration of unconjugated QDs, indicating that CPP promotes intracellular delivery of the conjugates. Furthermore, the green fluorescence is distributed within the perinuclear region of the cells. Punctate QD fluorescence is dispersed in the cell cytoplasm as well as in close proximity to the cell nuclei. These results provide strong evidence that conjugating CPP to QDs allows for cellular internalization, presumably via endocytotic uptake.

Figure 7:
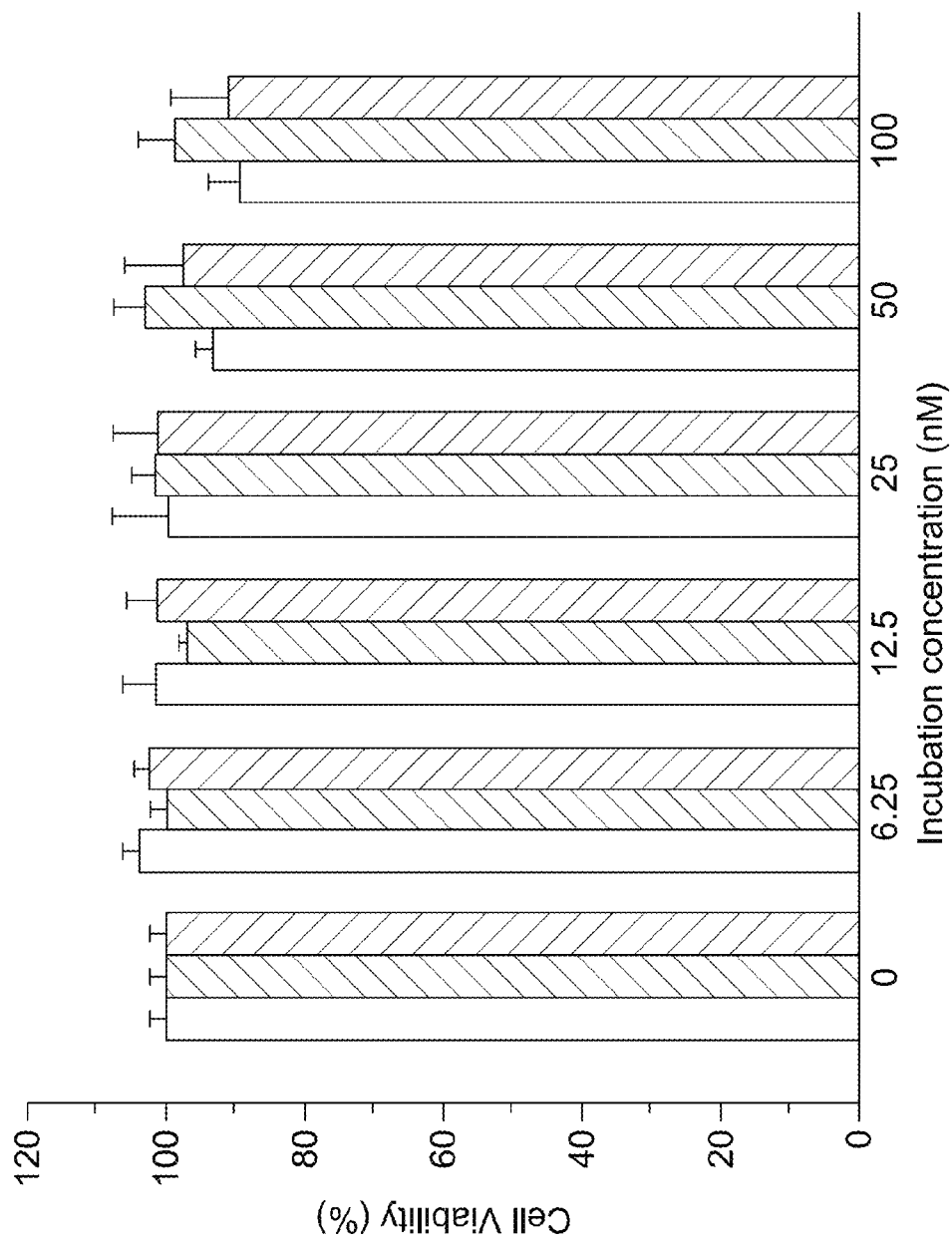
FIG. 7 is a chart of MTT viability tests of HeLa cells incubated for 24 hours with varying concentrations of QDs ligated with the three sets of polymers: LA-PIMA-PEG (left bar of each trio, clear), His-PIMA-PEG (center bar of each trio, upward sloping hash), and LA-His-PIMA-PEG (right bar of each trio, downward sloping has). QDs emitting at 537 nm have been used.

We also assessed the cytotoxicity of QDs ligated with LA-PIMA-PEG, His-PIMA-PEG and LA/His-PIMA-PEG to HeLa cells following 24-hour incubation using MTT assay. See FIG. 7, which is a chart of MTT viability tests of HeLa cells incubated for 24 hours with varying concentrations of QDs ligated with the three sets of polymers: LA-PIMA-PEG (left bar of each trio, clear), His-PIMA-PEG (center bar of each trio, upward sloping hash), and LA-His-PIMA-PEG (right bar of each trio, downward sloping has). QDs emitting at 537 nm have been used. The data show that the viability of cells incubated with QDs coated with these three sets of ligands essentially remained at 100% throughout the conjugate concentrations used (0 to 100 nM). These findings indicate that overall QDs capped with the polymer ligands containing PEG moieties induce minimal to no toxicity to cell cultures.

VI. Conclusion

We have designed and optimized a set of multi-coordinating amphiphilic polymer ligands ideally suited for surface-functionalizing QDs. The ligand design relies on the specific and highly efficient nucleophilic addition between poly (isobutylene-alt-maleic anhydride) and a set of amine-modified target functions. Using this synthetic platform, we were able to introduce large but controllable numbers of anchoring, hydrophilic and reactive groups onto a PIMA chain. In particular, we have combined two distinct metal-coordinating groups, dihydrolipoic acid and imidazole, along with PEG moieties within the same ligand. This combination provides additional flexibility and addresses issues of quenching and potential oxidation of thiol-based ligands and weak binding affinity of imidazole-based ligands. We further combine this ligand design with a mild photoligation strategy to promote the in-situ ligand exchange and phase transfer of hydrophobic QDs to aqueous media under borohydride-free conditions.

This strategy yields compact polymer-capped QDs that exhibit great colloidal stability over a broad range of conditions, such as pH 3-13, in high ionic strength buffer, in the presence of dithiothreitol, and in cell growth media. Furthermore, hydrophilic dispersions of polymer-coated QDs at very low concentration (10 nM) that are colloidally stable under ambient conditions (room temperature and light exposure) have been prepared and tested. This result is promising for fluorescent labeling in biology, such as intracellular imaging and sensing, where very small reagent concentrations are often required. We also show that these QDs can be functionalized with reactive dye, redox-active dopamine and cell penetrating peptide using conventional coupling strategies. Furthermore, MTT viability assays indicate that these polymer-ligated QDs elicit little to no cytotoxicity. Finally, we would like to stress that the present multifunctional polymer platform is ideally adapted for orthogonal chemistry, as one can easily introduce at least two different reactive groups (e.g., carboxy-plus-amine, carboxy-plus-azide, carboxy-plus-amine and biotin) during the nucelophilic addition step and without requiring addition post synthesis steps. In addition, the present ligand design can be easily adapted to a variety of other inorganic nanocrystals, such as iron oxide and metal nanoparticles, by replacing the metal chelating groups.

EXAMPLES

The following non-limiting examples are provided to further illustrate the present invention.

Example 1. Materials

Poly(isobutylene-alt-maleic anhydride) (PIMA) (average Mw: 6000 Da), Poly(ethylene glycol) (PEG) (average Mw: 600 Da), poly(ethylene glycol) methyl ether (average Mw: 750 Da), dopamine hydrochloride, dimethylformamide (DMF), triethylamine, lipoic acid, sodium azide, RPMI-1640 growth media, along with most of the chemicals used were purchased from Sigma Aldrich (St Louis, Mo.). Sulfo-Cy3 NHS ester and PD10 columns were purchased from Lumiprobe (Hallandale Beach, Fla.). Solvents were purchased from Sigma Aldrich (St Louis, Mo.). Column purification chromatography was performed using silica gel (60 Å, 230-400 mesh) acquired from Bodman Industries (Aston, Pa.). Deuterated solvents used for NMR experiments were purchased from Cambridge Isotope Laboratories (Andover, Mass.). The chemicals and solvents were used as received unless otherwise specified. All syntheses were carried out under N2 passed through an O2 scrubbing tower unless otherwise stated. Air sensitive materials were handled in an MBraun Labmaster glovebox, and standard Schlenk techniques were used in manipulation of air-sensitive solutions.

Example 2. Characterization $^1$H NMR spectra of the ligands were recorded using a 600 MHz spectrometer (Bruker SpectroSpin, Billerica, Mass.). Transmission electron microscopy (TEM) images were taken using a 200 kV JEOL-2010 instrument or a Philips FEI CM-120 operating at an acceleration voltage of 120 kV. Samples for TEM were prepared by drop casting the NP dispersion onto the holey carbon film on a fine mesh Cu grid (400 mesh). Dynamic light scattering measurements were carried out using ALV/CGS-3 Compact Goniometer System (ALV-GmbH, Langen, Germany). This system is equipped with a HeNe laser (illuminated at 632.8 nm), ALV photon correlator and an avalanche photodiode for signal detection. The scattered signal can be detected at angles ranging from 15 to 150 degrees. Each scattered pattern used for analysis was the average result of 3 acquisition periods of 10 seconds each. FT-IR spectra of the purified compounds were collected using a Spectrum 100 FTIR Spectrometer (PerkinElmer, Waltham, Mass.). Optical absorption data of dye-conjugated NPs was collected using an UV-Vis absorption spectrophotometer (UV 2450 model, Shimadzu, Columbia, Md.). The fluorescence spectra were collected using a Fluorolog-3 spectrofluorometer (HORIBA Jobin Yvon, Edison, N.J.) equipped with PMT and CCD detectors. Solvent evaporation was carried using a rotary evaporator R-215 (Buchi, New Castle, Del.). The absorption data for the MTT assay were collected using a microplate reader (Infinite M1000 from Tecan, Durham, N.C.).

Example 3. Synthesis of LA/His-PIMA-PEG (30% His, 20% LA and 50% PEG)

0.385 g of Poly(isobutylene-alt-maleic anhydride) (PIMA, Mw~6000 g/mol, 2.5 mmol monomer units) was dissolved in 10 mL of dry DMF using a 50 mL three-necked round-bottomed flask equipped with an addition funnel and a magnetic stirring bar. The solution was purged with nitrogen and then heated up to 40° C. Separately, two vials, one containing a mixture of LA-NH$_2$ (0.124 g, 0.5 mmol) and H$_2$N-PEG-OMe (0.47 g, 0.625 mmol) dissolved in 2 mL of DMF and the other containing histamine (0.0834 g, 0.75 mmol) and H$_2$N-PEG-OMe (0.47 g, 0.625 mmol) in 2 mL of DMF were prepared. The content of each vial was loaded separately into the addition funnel and added dropwise to the PIMA solution. When the addition was complete, the reaction mixture was left stirring overnight at 40° C. The solvent was removed under vacuum and then chloroform (3 mL) was added. The solution was loaded onto a silica column and the compound was purified with chloroform as the eluent to collect the final product (as a yellow gel), with a yield-91%.

Example 4. Synthesis of LA/His-PIMA-PEG-R (30% His, 20% LA, 50% PEG and 5% Amine)

0.385 g of PIMA (2.5 mmol monomer units) dissolved in 10 mL of dry DMF was added into 50 mL three-necked round-bottomed flask equipped with an addition funnel; the solution was heated up to 40° C. while stirring. To the flask, 2 mL of DMF solution containing LA-NH$_2$ (0.124 g, 0.5 mmol) and H$_2$N-PEG-OMe (0.28 g, 0.375 mmol) was added dropwise through the addition funnel Following that, 2 mL of DMF solution containing histamine (0.0834 g, 0.75 mmol) and H$_2$N-PEG-OMe (0.28 g, 0.375 mmol) was added also dropwise, and the mixture was left stirring for 1 hour. Then, H$_2$N-PEG-NH$_2$ (0.075 g, 0.125 mmol) and H$_2$N-PEG-OMe (0.28 g, 0.375 mmol) dissolved in 2 mL of DMF were finally added to flask. Once the addition was complete, the reaction mixture was left stirring at 40° C. overnight, and then the solvent was removed under vacuum. The ligand was further purified onto a silica column and chloroform was used as the eluent to collect the final product, with a yield ~85%.

Example 5. Growth of CdSe—ZnS Core-Shell Quantum Dots

The QD samples were prepared in two reaction steps via reduction of organometallic precursors at high temperature in a hot coordinating solvent mixture. The CdSe core was gown first via reduction of cadmium and selenium precursors at temperature of ~300-350° C. using a coordinating solvent mixture made of trioctyl phosphine (TOP), trioctyl phosphine oxide (TOPO) and alkylamines along with a small fraction hexylphosphonic acid; the CdSe nanocrystal size was controlled via small adjustments in the precursor concentrations and annealing temperature. See References 2, 3, and 7. Overcoating the CdSe core with a shell made of a few monolayers (here ~5-6) of ZnS using zinc and sulfur precursors, but the procedure was carried out at lower temperature (150-180° C.). See References 8-10. All QDs were prepared to have similar overcoating ZnS layer; the overall core-shell size difference is primarily due to variation in the core radius.

Example 6. Ligand Exchange of Quantum Dots with his-PIMA-PEG

150 µL of hydrophobic QDs (26.7 µM) were precipitated using ethanol (or a mixture of methanol and butanol) and redispersed in 100 µL of THF. Then 25 mg of His-PIMA-PEG dissolved in 150 µL of THF was added to the QD solution; a homogeneous solution resulted. The vial was sealed with a rubber septum, and the atmosphere was switched to nitrogen by applying 2 to 3 rounds of mild vacuum, followed by purging with nitrogen. The solution was heated to 40° C., and then left stirring for 2 hours. The QD samples were precipitated by adding excess (~5 mL) hexane and centrifuged at 3700 RPM for 5 min yielding a yellow pellet. The clear supernatant was discarded, and the pellet redissolved in 200 µL of THF, followed by another round of precipitation using excess hexane. The precipitate was dried under vacuum, then dispersed in DI water. After sonication, the clear aqueous dispersion was filtered through a 0.45 µm disposable syringe filter, and the excess free ligands were removed by applying a 3-4 rounds of concentration/dilution using a centrifugal filtration device (Millipore, Mw cutoff=50 kDa). This afforded clear QD solution with final volume of ~500 µL and a concentration of ~7-8 µM, as estimated from the absorption data and the extinction coefficient of the QD material. See Reference 72.

Example 7. Ligand Exchange of Quantum Dots with his/LA-PIMA-PEG

The above procedure can also be applied to His/LA-PIMA-PEG ligand. This yields hydrophilic QDs where the imidazole groups drive the coordination onto the QD surfaces, while the lipoic acids (in the form of dithiolanes) stay free and laterally exposed for potential additional transformation targeting the dithiolane ring (see FIG. 2).

Example 8. Photoligation of Quantum Dots with LA-PIMA-PEG

The phase transfer of the QDs with LA-containing ligands was carried using a photoligation strategy we have recently developed. See Reference 60. Here, cap exchange of the LA groups is photochemically-induced under borohydride-free conditions. This procedure was carried out by UV photo-irradiation of the hydrophobic QDs mixed with LA-containing polymer(s). Briefly, QDs (26.7 μM, 150 μL) were precipitated using ethanol and redispersed in 100 μL of THF. Then 200 μL of THF containing LA-PIMA-PEG (25 mg) was mixed with the QD solution, followed by the addition of 30 μL of tetramethylammonium hydroxide (~5 mM) pre-dissolved in methanol. The vial was sealed with a rubber septum, and the atmosphere was switched to nitrogen by applying 2 to 3 rounds of mild vacuum followed by flushing with nitrogen. The vial was then placed inside the UV photoreactor and irradiated for 20 min (at 350 nm, 4.5 mW/cm$^2$) with stirring. Hexane was then added to precipitate out the QDs. The sample was centrifuged at 3700 RPM for 5 min and the precipitated pellet was redispersed in 200 μL of THF. Another round of precipitation with excess hexane was applied, and the resulting QD pellet was dried under vacuum and dispersed in DI water. The aqueous dispersion was then filtered through a 0.45 μm syringe filter and purified by applying 3-4 rounds of concentration/dilution using a membrane filtration device Amicon Ultra 50 kDa (from Millipore) to remove excess ligands.

Example 9. Photo-Mediated Ligand Exchange with LA/his-PIMA-PEG

QDs (26.7 μM, 150 μL) were precipitated using ethanol and dispersed in 100 μL of THF. This solution was mixed with 200 μL of THF containing 25 mg of LA/His-PIMA-PEG. The vial was sealed with a rubber septum, purged with nitrogen, and the solution was stirred for 2 hours at 40° C. 30 μL of tetramethylammonium hydroxide (~5 mM) dissolved in ethanol was added, followed by UV irradiation (using the UV reaction) for 10 min. Two rounds of precipitation with excess hexanes were applied and the QD pellet was dried under vacuum and dispersed in DI water. The aqueous dispersion was then filtered through a syringe filter and further purified by applying 3-4 rounds of concentration/dilution (Mw cutoff=50,000). Alternatively, the phase transfer of QDs to DI water can be carried out before performing the UV irradiation. Briefly, following precipitation of the native QDs with ethanol and centrifugation, the pellet of TOP/TOPO-QDs was dispersed in 100 μL of THF and mixed with 25 mg of LA/His-PIMA-PEG pre-dissolved in 200 μL of THF. The mixture was left stirring for 2 hours and precipitated with excess hexane. The precipitated QD pellet was dried under vacuum and dispersed in 200 μL of DI water. 30 μL of tetramethylammonium hydroxide (~5 mM) dissolved in water was introduced, followed by UV irradiation for 10 min. The QDs were filtered through a 0.45 μm syringe filter, and purified by applying 3-4 rounds of concentration/dilution using a membrane filtration device as done above.

Example 10. NMR Characterization of the Hydrophilic QDs

Figure 3B:
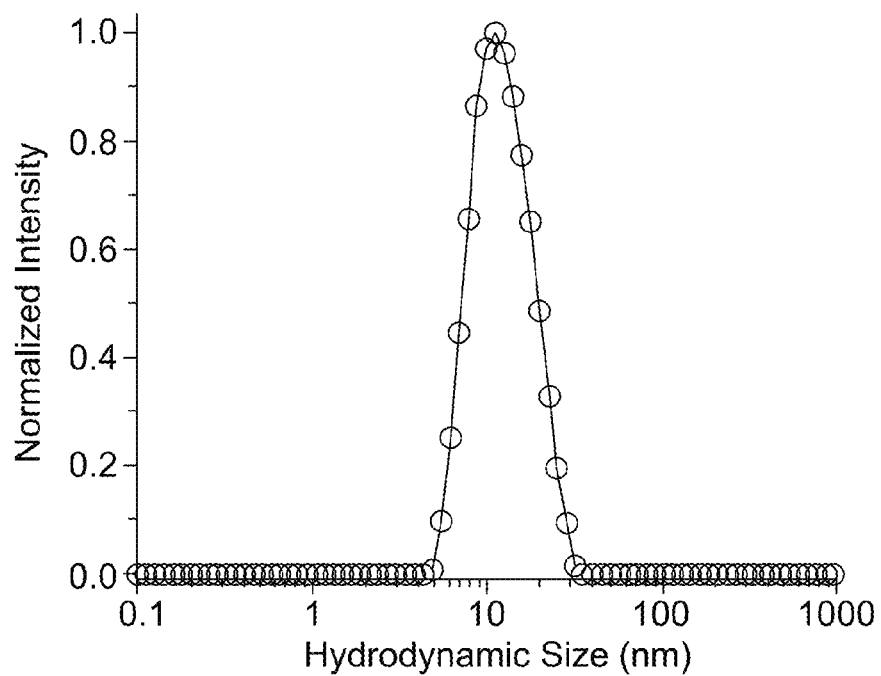
FIG. 3B is a histogram showing the distribution of the intensity vs. hydrodynamic radius, extracted from the Laplace transform of the auto-correlation function shown in FIG. 3A.

We used pulsed field gradient water suppression $^1$H NMR to collect our spectra. The solvent was switched from hydrogenated DI water to deuterated water by applying two rounds of concentration/dilution using 2 mL of D$_2$O each. The final volume of the dispersion in D$_2$O used to collect the spectra was adjusted to 450 μL. For instance, the spectra shown in FIG. 3 were collected using a dispersion of LA/His-PIMA-PEG-QDs at a concentration of 18 μM and averaged over 500 scans. The sample used for the ligand counting experiments was prepared following the same protocol, except that 0.6 μL pyridine (7.45 μmol) was added to provide a standard/reference to which the signature of the polymer-capped QDs will be compared. We also characterize the filtrate collected in the bottom of the device using $^1$H NMR spectroscopy. We have found no sign of free ligands in the filtrates, as the purification steps are able to reduce the concentration of excess ligands to below the detection limit of the instrument.

Example 11. Conjugation of Amine-QDs to Cy3 Dye

Green-emitting QDs ligand-exchanged with LA/His-PIMA-PEG-NH$_2$ were reacted with sulfo-Cy3 NHS ester to provide QD-dye conjugates. Briefly, 117 μL of amine-functionalized QDs (8.52 μM) were dispersed in 373 μL of phosphate buffer (50 mM, pH=8.0), and then 15 equiv. of activated sulfo-Cy3 NHS ester dye dissolved in DMSO (at 1.5 mM in 10 μL), was added. The reaction mixture was left to proceed for ~1.5 hour at room temperature, then the QD-dye conjugates were separated from unbound dye and NHS byproduct via size exclusion chromatography (using PD 10 column); the first eluted fraction of QD-dye conjugates was characterized using absorption and fluorescence measurements.

Example 12. Assembly of the QD-Dopamine Conjugates

To a vial containing 1 mL of DI water, we added 94 μL of amine-functionalized QDs (concentrations=8.52 μM) and 11 μL of dopamine-isothiocyanate (dopamine-ITC) pre-dissolved in DMSO (0.5 mg/mL). The dopamine-ITC was prepared in our laboratory following previous protocols. See Reference 24. The mixture was stirred for 3-3.5 h in the dark, followed by removal of excess free/unreacted dopamine by applying one round of concentration/dilution using a membrane filtration device (Mw cutoff: 50 kDa, Millipore); DI water was then added to the purified materials to provide a stock dispersion of QD-conjugates with a concentration of ~0.8 μM. Aliquots (40 μL) of this stock dispersion were then mixed with 960 μL of phosphate buffer (10 mM) at the desired pH (e.g., pH 4-10). These conjugates were then used to collect the steady-state florescence and time-resolved fluorescence data.

Example 13. Assembly of the QD-CPP Conjugates

To prepare QD-CPP conjugates, the carboxylic groups (freed during the addition reaction) available on the surface of QDs ligated with LA/His-PIMA-PEG were targeted for coupling with amine-terminated CPP via EDC/NHS reaction. See Reference 51. Briefly, 100 μL of QDs (9.3 μM) were dispersed in 400 μL of phosphate buffer (50 mM, pH=6.5), and then 50 equiv. of NHS (8.5 mM, 6 μL) and EDC (5 mM, 10 μL) in aqueous solution were added. The reaction was left to proceed for ~1.5 hour at room temperature, then the excess EDC and NHS were removed using one round of concentration/dilution with DI water through a membrane filtration device (Mw cutoff: 50 kDa, Millipore). The purified QD-NHS esters were added to 400 μL of phosphate buffer (50 mM, pH=8.0) containing ~5-fold excess of CPPs (4.6 mM, 1 μL) with respect to QDs. The mixture was left to react at room temperature for 2 hours. The conjugates were separated from unbound CPP and NHS byproduct via size exclusion chromatography (using PD 10 column); the first eluted fraction containing the QD-CPP conjugates was used for the cellular uptake experiments.

Example 14. Fluorescence Imaging of Live Cells

HeLa cell cultures (human cervix carcinoma cell line, provided by the FSU cell culture facility) were grown at 37° C. in a humidified 5% $CO_2$ atmosphere at 37° C., as a monolayer in a complete growth medium (Dulbecco's Modified Eagle's Medium, DMEM, Cellgro), supplemented with 10% (v/v) fetal bovine serum (Gibco), 4.5 g/L glucose, L-glutamine, sodium pyruvate, 1% (v/v) antibiotic-antimycotic 100× (Gibco), and 1% (v/v) non-essential amino-acid solution 100× (Sigma). $8 \times 10^4$ of the above cells were first seeded onto 12 mm circle micro-cover glasses (VWR) for 24-well microplates (CellStar, VWR), and the plates were placed in an incubator overnight to allow for cell attachment. After 24 h, the cells were mixed with the QD-CPP conjugate (at a concentration of 200 nM) and left to incubate for 1 hour. After incubation the cells were washed with PBS buffer two times, fixed with 3.7% paraformaldehyde and stained with 4,6-diamino-2-phenylindole (Prolong Antifade mounting media with DAPI nuclear staining, Invitrogen). Control experiments were carried out by incubating the cells with unconjugated QDs (without CPP). The fluorescence images were acquired using an Inverted Research Nikon Eclipse Ti Microscope equipped with a color CoolSNAP HQ2 CCD camera. Excitation of the sample was provided by a Xe lamp, while the fluorescence images were collected using a 40× objective (Nikon) and a set of filter cubes (Chroma Technology (Rockingham, Vt.). DAPI fluorescence was detected using a DAPI cube (with 340-380 nm excitation and 435-485 nm emission line). The QD fluorescence signal (peak at 540 nm) was detected using a GFP/EGFP cube (with 465-495 nm excitation and 515-555 nm emission line).

Example 15. Viability Assays

The viability of HeLa cells incubated with QDs capped with LA-PIMA-PEG, His-PIMA-PEG and LA/His-PIMA-PEG ligands at concentrations of 0, 6.25, 12.5, 25, 50 and 100 nM, were tested using MTT (3-(4,5-dimethylthiazol-2-yl)-2,5-diphenyltetrazolium bromide) assay. MTT assay is a colorimetric test based on the cellular reduction of MTT (Sigma Aldrich Chemical) by the mitochondrial dehydrogenase of viable cells, forming a blue formazan product which can be measured spectrophotometrically. MTT solution was prepared at 5 mg/mL in PBS 1× and then diluted 1:5 in medium without serum or Phenol Red. Cells were first seeded into 96-well microplates ($2 \times 10^4$ cells/200 μL/well), and the microplates were placed in an incubator overnight to allow adherence. Dispersions of QDs were then applied directly to the wells using a multichannel pipette (in triplicate), and the cultures were incubated for 24 h at 37° C. After incubation, the media was removed, the cells washed twice with PBS 1×, then 200 μL of the MTT solution (0.2 mg/mL) was added to each well and left to incubate for 4 h at 37° C. The MTT solution was removed, and 100 μL of 100% DMSO was added to each well to solubilize the MTT-formazan product. Absorbance at 560 nm was measured using a plate reader (the Infinite M1000 PRO from TECAN). The cell viability obtained from the absorbance measurements was expressed as a fraction of viable cells and normalized to that of cells that were not exposed to the QDs.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed is:

1. A composition comprising a polymer comprising repeat unit (A') and repeat unit (B), as represented by the following structures:

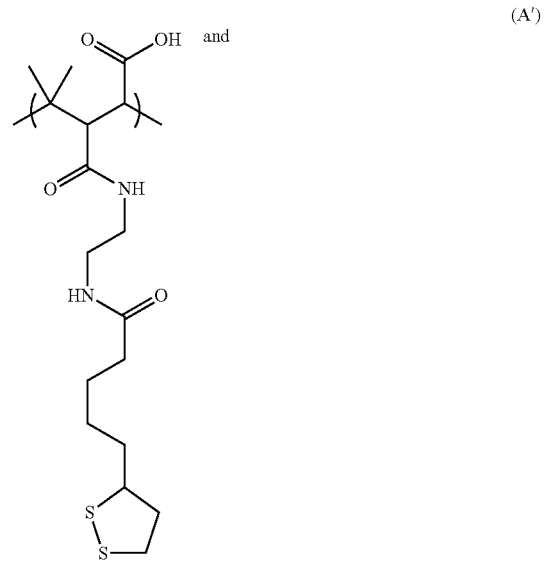

(A') and

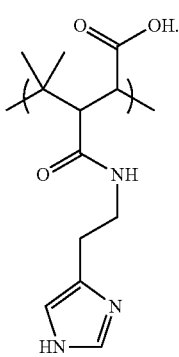
(B)

2. The composition of claim 1 wherein the polymer further comprises repeat unit (C)₂ as represented by the following structure:

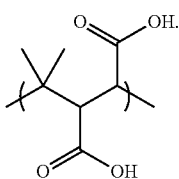
(C)

3. The composition of claim 1 wherein the polymer further comprises repeat unit (D), as represented by the following structure:

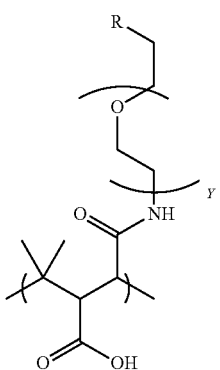
(D)

wherein Y has a value between one and about 100 and each R is independently selected from the group consisting of hydroxy (—OH), methoxy (—OCH₃), amino (—NH₂), azido (—N₃), thiol (—SH), lipoic acid, ethynyl (—C≡CH), carboxyl (—COOH), aldehyde (—C(O)H), maleimide, and biotin.

4. The composition of claim 1 wherein the polymer comprises a coating over a nanoparticle.

5. The composition of claim 4 wherein the nanoparticle comprises a magnetic material.

6. The composition of claim 4 wherein the nanoparticle comprises a material selected from the group consisting of Fe₃O₄, Fe₂O₃, FePt, Co, Mn-doped Fe₃O₄, CdSeS/ZnS, InP/ZnS, PbS, CdTe, CoPt, FeCoPt, CoFe₂O₄, MnO, Mn₃O₄, Co₃O₄, FeO, Ni, TiO₂, Al₂O₃, CdSe, PbSe, ZrO₂, ZnO, Au, Ag, and graphene oxide.

7. A composition comprising a polymer comprising repeat unit (A″) and repeat unit (B), as represented by the following structures:

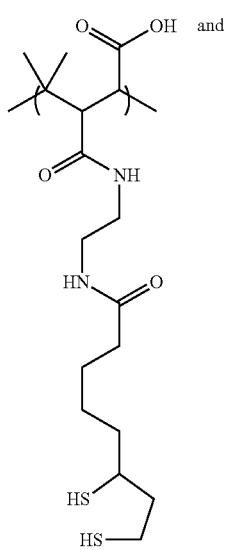
(A″) and

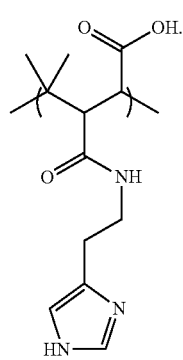
(B)

8. The composition of claim 7 wherein the polymer further comprises repeat unit (C), as represented by the following structure:

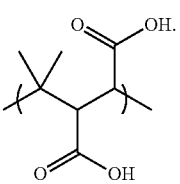
(C)

9. The composition of claim 7 wherein the polymer further comprises repeat unit (D), as represented by the following structure:

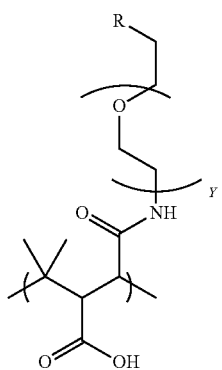

(D)

wherein Y has a value between one and about 100 and each R is independently selected from the group consisting of hydroxy (—OH), methoxy (—OCH$_3$), amino (—NH$_2$), azido (—N$_3$), thiol (—SH), lipoic acid, ethynyl (—C≡CH), carboxyl (—COOH), aldehyde (—C(O)H), maleimide, and biotin.

10. The composition of claim 7 wherein the polymer comprises a coating over a nanoparticle.

11. The composition of claim 10 wherein the nanoparticle comprises a magnetic material.

12. The composition of claim 10 wherein the nanoparticle comprises a material selected from the group consisting of Fe$_3$O$_4$, Fe$_2$O$_3$, FePt, Co, Mn-doped Fe$_3$O$_4$, CdSeS/ZnS, InP/ZnS, PbS, CdTe, CoPt, FeCoPt, CoFe$_2$O$_4$, MnO, Mn$_3$O$_4$, Co$_3$O$_4$, FeO, Ni, TiO$_2$, Al$_2$O$_3$, CdSe, PbSe, ZrO$_2$, ZnO, Au, Ag, and graphene oxide.

13. A composition comprising a polymer comprising repeat unit (A'), repeat unit (A"), and repeat unit (B), as represented by the following structures:

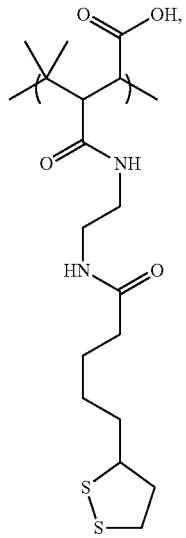

(A')

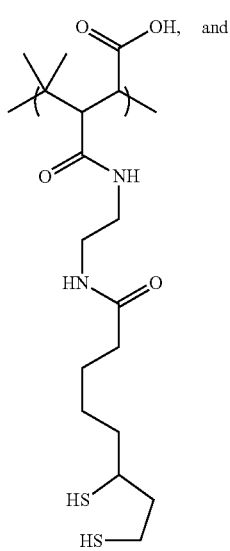

(A")

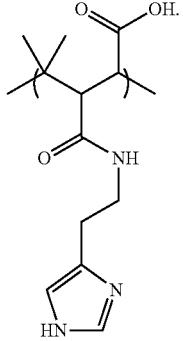

(B)

14. The composition of claim 13 wherein the polymer further comprises repeat unit (C), as represented by the following structure:

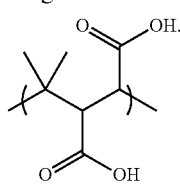

(C)

15. The composition of claim 13 wherein the polymer further comprises repeat unit (D), as represented by the following structure:

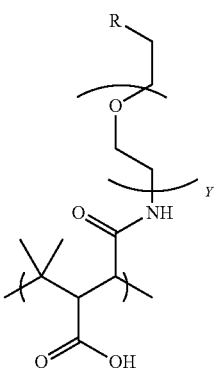

(D)

wherein Y has a value between one and about 100 and each R is independently selected from the group consisting of hydroxy (—OH), methoxy (—OCH$_3$), amino (—NH$_2$), azido (—N$_3$), thiol (—SH), lipoic acid, ethynyl (—C≡CH), carboxyl (—COOH), aldehyde (—C(O)H), maleimide, and biotin.

16. A method of preparing a polymer comprising repeat unit (A″) and repeat unit (B), as represented by the following structures:

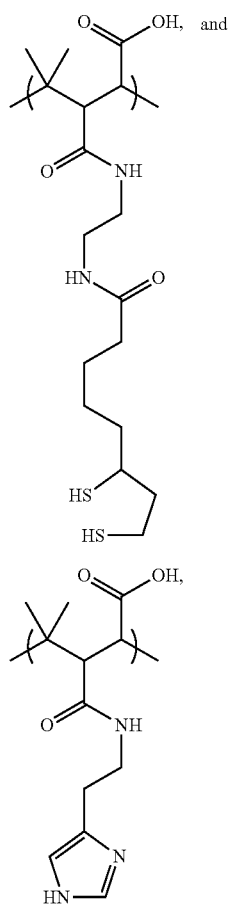

the method comprising contacting poly(isobutylene-alt-maleic anhydride) with N-(2-aminoethyl)-6,8-dimercaptooctanamide and histamine.

17. The method of claim 16 wherein the method comprises contacting poly(isobutylene-alt-maleic anhydride) and the amine-containing reactant with a compound having the structure:

H$_2$N$\{\}$O$\}_Y$R$_2$ wherein Y has a value between one and about 100 and each R$_2$ is independently selected from the group consisting of hydroxy (—OH), methoxy (—OCH$_3$), amino (—NH$_2$), azido (—N$_3$), thiol (—SH), lipoic acid, ethynyl (—C≡CH), carboxyl (—COOH), aldehyde (—C(O)H), maleimide, and biotin; wherein the polymer further comprises repeat unit (D):

* * * * *